(12) United States Patent
Keimel

(10) Patent No.: US 11,723,865 B2
(45) Date of Patent: *Aug. 15, 2023

(54) SYSTEMS AND METHODS FOR ENHANCED DISTRIBUTION OF A BIOLOGIC AGENT WITHIN THE BRAIN AND SPINAL CORD

(71) Applicant: New Hope Research Foundation, Inc., North Oaks, MN (US)

(72) Inventor: John G. Keimel, North Oaks, MN (US)

(73) Assignee: New Hope Research Foundation, Inc., North Oaks, MN (US)

( * ) Notice: Subject to any disclaimer, the term of this patent is extended or adjusted under 35 U.S.C. 154(b) by 297 days.

This patent is subject to a terminal disclaimer.

(21) Appl. No.: 16/784,902

(22) Filed: Feb. 7, 2020

(65) Prior Publication Data
US 2020/0276121 A1 Sep. 3, 2020

Related U.S. Application Data

(63) Continuation-in-part of application No. 15/891,879, filed on Feb. 8, 2018.

(60) Provisional application No. 62/802,611, filed on Feb. 7, 2019, provisional application No. 62/456,281, filed on Feb. 8, 2017.

(51) Int. Cl.
*A61K 9/00* (2006.01)
*C12N 15/86* (2006.01)
*A61K 45/06* (2006.01)

(52) U.S. Cl.
CPC .......... *A61K 9/0085* (2013.01); *A61K 9/0019* (2013.01); *C12N 15/86* (2013.01); *A61K 45/06* (2013.01); *C12N 2750/14143* (2013.01)

(58) Field of Classification Search
CPC .................................................... A61K 9/0085
See application file for complete search history.

(56) References Cited

U.S. PATENT DOCUMENTS

| | | | |
|---|---|---|---|
| 3,928,574 A | 12/1975 | Phillips | |
| 5,641,749 A * | 6/1997 | Yan | A61P 25/02 514/8.4 |
| 5,720,720 A | 2/1998 | Laske et al. | |

(Continued)

OTHER PUBLICATIONS

Ambuhl, P. M. et al., "Quantification and predictors of plasma volume expansion from mannitol treatment," Intensive Care Med (1997) 23: 1159-1164 (6 pages).

(Continued)

*Primary Examiner* — William R Carpenter
(74) *Attorney, Agent, or Firm* — Pauly, DeVries Smith & Deffner LLC

(57) ABSTRACT

Aspects herein relate to systems and methods for delivery of biologic agents to the central nervous system. In various embodiments, a method of administering a therapeutic agent to the central nervous system (CNS) is included. The method can include injecting a therapeutic agent into a first cerebrospinal fluid (CSF) region of the subject. The method can further include establishing fluid communication between a fluid reservoir and a second cerebrospinal fluid (CSF) region of a subject, the fluid having a hydraulic pressure at or above an intracranial pressure. The method can further include infusing a hyperosmotic fluid systemically. Other embodiments, including kits and systems are also included herein.

17 Claims, 13 Drawing Sheets

(56) References Cited

U.S. PATENT DOCUMENTS

| | | | |
|---|---|---|---|
| 5,736,157 A | 4/1998 | Williams | |
| 6,436,708 B1 * | 8/2002 | Leone | C12N 15/86 435/320.1 |
| 6,605,036 B1 | 8/2003 | Wild | |
| 7,442,372 B2 | 10/2008 | Kakkis et al. | |
| 8,419,710 B2 | 4/2013 | Keimel et al. | |
| 10,945,951 B2 * | 3/2021 | Verma | A61H 9/0092 |
| 11,541,005 B2 | 1/2023 | Keimel et al. | |
| 2005/0245880 A1 * | 11/2005 | Howlett | A61M 5/285 604/231 |
| 2006/0184098 A1 * | 8/2006 | Barnitz | A61M 25/007 604/43 |
| 2008/0140008 A1 | 6/2008 | Keimel et al. | |
| 2008/0140056 A1 | 6/2008 | Keimel et al. | |
| 2009/0312770 A1 * | 12/2009 | Kozai | A61B 5/291 606/129 |
| 2017/0216139 A1 | 8/2017 | Avery | |
| 2017/0360699 A1 * | 12/2017 | Verma | A61H 9/00 |
| 2018/0228970 A1 * | 8/2018 | Wostyn | A61K 35/30 |
| 2019/0038554 A1 | 2/2019 | Keimel | |

OTHER PUBLICATIONS

Belur, Lalitha et al., "Gene Delivery and Biodistribution in the Brain Following Adeno-Associated Virus Serotype 5 Vector-Mediated Gene Transfer," Molecular Therapy 2007 (15) S379 (1 page).

Bobo, R. H. et al., "Convection-enhanced delivery of macromolecules in the brain," Proc. Natl. Acad. Sci. USA vol. 91, pp. 2076-2080, Mar. 1994 (5 pages).

Boulton, M. et al., "Determination of volumetric cerebrospinal fluid absorption into extracranial lymphatics in sheep," Am J Physiol, 1998, vol. 274, pp. R8-96 (9 pages).

Boulton, M. et al., "Raised intracranial pressure increases CSF drainage through arachnoid villi and extracranial lymphatics," Am J Physiol, vol. 275. pp. R889-96, Sep. 1998 (8 pages).

Broekman, M.L.D. et al., "Adeno-Associated Virus Vectors Serotyped with AAV8 Capsid are More Efficient than AAV-1 or -2 Serotypes for Widespread Gene Delivery to the Neonatal Mouse Brain," Neuroscience 138(2006) 501-510 (10 pages).

Broekman, M.L.D et al., "Complete Correction of Enzymatic Deficiency and Neurochemistry in the GM1-gangliosidosis Mouse Brain by Neonatal Adeno-associated Virus-mediated Gene Delivery," Molecular Therapy 2007 vol. 15 No. 1 30-37 (8 pages).

Burger, Corinna et al., "Recombinant Adeno-Associated Viral Vectors in the Nervous System," Human Gene Therapy 16:781-791 Jul. 2005 (11 pages).

Burger, Corinna et al., "Systemic Mannitol-Induced Hyperosmolality Amplifies rAAV2-Mediated Striatal Transduction to a Greater Extent Than Local Co-infusion," Molecular Therapy vol. 11, No. 2, Feb. 2005 pp. 327-331 (5 pages).

Cartier, N. et al., "Lentiviral hematopoietic cell gene therapy for X-linked adrenoleukodystrophy," Methods Enzymol. vol. 507, pp. 187-198, 2012 (12 pages).

Cartier, Nathalie et al., "Hematopoietic Stem Cell Gene Therapy with a Lentiviral Vector in X-Linked Adrenoleukodystrophy," Science Nov. 6, 2009 vol. 326 pp. 818-823 (6 pages).

Carty, Nikisha et al., "Convection-Enhanced Delivery and Systemic Mannitol Increase Gene Product Distribution of AAV vectors 5, 8, and 9 and Increase Gene Product in the Adult Mouse Brain," J. Neurosci Methods. Dec. 15, 2010; 194(1): 144-153 (20 pages).

Chen, Michael Y. et al., "Surface properties more than size, limiting convective distribution of virus-sized particles and viruses in the central nervous system," J Neurosurg 103: 311-319, 2005 (9 pages).

Cloyd, J. C. et al., "Mannitol pharmacokinetics and serum osmolality in dogs and humans," J Pharmacol Exp Ther, vol. 236, pp. 301-306, Feb. 1986 (6 pages).

Crystal, R. G. et al., "Administration of a Replication-Deficient Adeno-Associated Virus Gene Transfer Vector Expressing the Human CLN2 cDNA to the Brain of Children with Late Infantile Neuronal Ceroid Lipofuscinosis," Human Gene Therapy 15:1131-1154, Nov. 2004 (24 pages).

Cserr, Helen F. et al., "Cervical lymphatics, the blood-brain barrier and the immunoreactivity of the brain: a new view," Immunol Today, vol. 13, No. 12 1992 pp. 507-512 (6 pages).

Cushing, H. "Some experimental and clinical observations concerning states of increased intracranial tension," American Journal of the Medical Sciences, vol. 124, pp. 375-400, Sep. 1902 (27 pages).

Cutler, R.W. et al., "Formation and absorption of cerebrospinal fluid in man," Brain, vol. 91, pp. 707-720, 1968 (14 pages).

Daly, Thomas M. et al., "Neonatal Gene transfer leads to widespread correction of pathology in a murine model of lysosomal storage disease," Proc. Natl. Acad. Sci. USA (1999) vol. 96 pp. 2296-2300 (5 pages).

Davidson, Beverly L. et al., "Recombinant adeno-associated virus type 2, 4, and 5 vectors: Transduction of variant cell types and regions in the mammalian central nervous system," PNAS 2000, vol. 97, No. 7 pp. 3428-3432 (5 pages).

Davson, H. et al., "Physiology of the CSF and Blood-Brain Barriers.," Boca Raton: CRC Press, 1996. p. 201 and Table 4.2 (2 pages).

Doran, Stephen et al., "Gene Expression from Recombinant Viral Vectors in the Central Nervous System after Blood-Brain Barrier Disruption," Neurosurgery 36(5), May 1995, p. 965-970 (14 pages).

Duque, Sandra et al., "Intravenous administration of self-complementary AAV9 enables transgene delivery to adult motor neurons," Mol. Ther. vol. 17, pp. 1187-1196 Jul. 2009 (10 pages).

Enzmann, Dieter R. et al., "Normal Flow Patterns of Intracranial and Spinal Cerebrospinal Fluid Defined with Phase-Contrast Cine MR Imaging," Radiology 1991; 178:467-474 (8 pages).

FDA, "Guidance for Industry: Gene Therapy Clinical Trials—Observing Subjects for Delayed Adverse Events," Federal Register vol. 71, No. 228, 2006 pp. 68821-68822 (2 pages).

Foust, Kevin D. et al., "Intravascular AAV9 preferentially targets neonatal-neurons and adult-astrocytes in CNS," Nat Biotechnol. Jan. 2009; 27(1): 59-65 (15 pages).

Fu, H et al., "Significantly increased lifespan and improved behavior performances by rAAV gene delivery in adult mucopolysaccharidosis IIIB mice," Gene Therapy (2007) 13, 1065-1077 (13 pages).

Fu, H. et al., "Restoration of central nervous system alpha-N-acetylglucosaminidase activity and therapeutic benefits in mucopolysaccharidosis IIIB mice by a single intracisternal recombinant adeno-associated viral type 2 vector delivery," J Gene Med, vol. 12, pp. 624-633, Jul. 2010 (10 pages).

Fu, Haiyan et al., "Correction of Neurological Disease of Mucopolysaccharidosis IIIB in Adult Mice by rAAV9 Trans-Blood-Brain Barrier Gene Delivery," Molecular Therapy 2011 vol. 19, No. 6 pp. 1025-1033 (9 pages).

Fu, Haiyan et al., "Self-Complementary Adeno-associated Virus Serotype 2 Vector: Global Distribution and Broad Dispersion of AAV-Mediated Transgene Expression in Mouse Brain," Molecular Therapy vol. 8, No. 6, Dec. 2003 pp. 911-917 (7 pages).

Garcia-Morales, E.J. et al., "Osmole gap in neurologic neurosurgical intensive care unit: Its normal value, calculation, and relationship with mannitol serum concentrations," Crit Care Med, vol. 32, pp. 986-991, Apr. 2004 (6 pages).

Gerlowski, Leonard E. et al., "Physiologically Based Pharmacokinetic Modeling: Principles and Applications," Journal of Pharmaceutical Sciences 1983; vol. 72 No. 10 pp. 1103-1127 (8 pages).

Ghodsi, Abdi et al., "Systemic Hyperosmolality Improves B-Glucuronidase Distribution and Pathology in Murine MPS VII Brain Following Intraventricular Gene Transfer," Experimental Neurology 160, 109-116 (1999) (8 pages).

Gray, S.J. et al., "Global gene delivery to the central nervous system via adeno-associated virus vectors administered intravenously," Abstract only. Society for Neuroscience, Chicago, Illinois, 2009 (1 page).

Gray, Steven J. et al., "Preclinical Differences of Intravascular AAV9 Delivery to Neurons and Glia: A Comparative Study of Adult Mice and Nonhuman Primates," Molecular Therapy 2011 vo. 19 No. 6. pp. 1058-1069 (12 pages).

(56) References Cited

OTHER PUBLICATIONS

Greitz, D. "Cerebrospinal fluid circulation and associated intracranial dynamics. A radiologic investigation using MR imaging and radionuclide cisternography," Neuroradiology and Radiation Physics, Karolinska Hospital, Stockholm, Sweden, 1993 (21 pages).
Griffey, Megan et al., "Adeno-associated virus 2-mediated gene therapy decreases autofluorescent storage material and increases brain mass in a murine model of infantile neuronal ceroid lipofuscinosis," Neurobiology of Disease 16 (2004) 360-369 (10 pages).
Habgood, Mark et al., "Delivering drugs into the brain: barriers and possibilities," Therapeutic Delivery (2010) 1(4), 483-488 (6 pages).
Hadaczek, Piotr et al., "Eight Years of Clinical Improvement in MPTP-Lesioned Primates After Gene Therapy With AAV2-hAADC," Molecular Therapy vol. 18 (2010) pp. 1458-1461 (4 pages).
Hocquemiller, Michael et al., "Adeno-Associated Virus-Based Gene Therapy for CNS Diseases," Human Gene Therapy (2016), vol. 27, No. 7 pp. 478-496 (19 pages).
Janson, Christopher et al., "Gene Therapy of Canavan Disease: AAV-2 Vector for Neurosurgical Delivery of Aspartoacylase Gene (ASPA) to the Human Brain," Human Gene Therapy 13: 1391-1412 (Jul. 20, 2002) (22 pages).
Janson, Christopher G. et al., "Comparison of Endovascular and Intraventricular Gene Therapy with Adeno-Associated Virus a-L-iduronidase for Hurler Disease," Neurosurgery. Jan. 2014; 74(1): 99-111 (26 pages).
Johanson, C.E. et al., "Multiplicity of cerebrospinal fluid functions: New challenges in health and disease," Cerebrospinal Fluid Res, vol. 5, p. 10, 2008 (35 pages).
Kalburgi, Sahana N. et al., "Recent Gene Therapy Advancements for Neurological Diseases," Discov Med. Feb. 2013; 15(81): 111-119 (15 pages).
Kaneda, Kotaro et al., "Pharmacokinetic Characteristics of Bolus-Administered Mannitol in Patients Undergoing Elective Craniotomy," J Clin Pharmacol 2010; 50:536-543 (8 pages).
Kang, Lu et al., "Long-Term CNS and Somatic Correction in MPS II Mice after Intrathecal Delivery of AAV9 Vector," Molecular Therapy 2007, vol. 15 S37 (1 page).
Karumuthil-Melethil, Subha et al., "Novel Vector Design and Hexosaminidase Variant Enabling Self-Complementary Adeno-Associated Virus for the Treatment of Tay-Sachs Disease," Human Gene Therapy 2016, vol. 27, No. 7 pp. 509-521 (13 pages).
Keimel, J. G. et al., "Intrathecal continuous or intermittent bolus delivery of Taronidase results in elevated levels in canine CNS tissue," Presented at the Lysosomal Disease Network WORLD Conference, Orlando, Florida 2006. Abstracts—Molecular Genetics and Metabolism 92 (2007) S11-S34 (2 pages).
Leone, P. et al., "Aspartoacylase Gene Transfer to the Mammalian Central Nervous System with Therapeutic Implications for Canavan Disease," Annals of Neurology vol. 48 No. 1, Jul. 2000 pp. 27-38 (12 pages).
Linninger, A. A. et al., "A mathematical model of blood, cerebrospinal fluid and brain dynamics," J Math Biol (2009) 59:729-759 (31 pages).
Linninger, Andreas A. et al., "Prediction of convection-enhanced drug delivery to the human brain," Journal of Theoretical Biology 250 (2008) 125-138 (14 pages).
Linninger, Andreas A. et al., "Rigorous Mathematical Modeling Techniques for Optimal Delivery of Macromolecules to the Brain," IEEE Transactions on Biomedical Engineering, vol. 55, No. 9, Sep. 2008 (2303-2313) (11 pages).
Liu, Gumei et al., "Functional Correction of CNS Phenotypes in a Lysosomal Storage Disease Model Using Adeno-Associated Virus Type 4 Vectors," The Journal of Neuroscience (2005) 25(41): 9321-9327 (7 pages).
Lofgren, Jan et al., "Cranial and Spinal Components of the Cerebrospinal Fluid Pressure-volume curve," Acta Neurol Scandinav. 1973; 49:575-585 (11 pages).

Louboutin, Jean-Pierre et al., "Efficient CNS Gene Delivery by Intravenous Injection," Nature Methods 2010, vol. 7 No. 11, pp. 905-907 (5 pages).
Mah, C et al., "Sustained Correction of Glycogen Storage Disease Type II Using Adeno-Associated Virus Serotype 1 Vectors," Gene Therapy (2005) pp. 1-5 (5 pages).
Martino, S. et al., "A Direct Gene Transfer Strategy Via Brain Internal Capsule Reverses the Biochemical Defect in Tay-Sachs Disease," Human Molecular Genetics, vol. 14, No. 15 (2005), pp. 2113-2123.
Mastakov, Mihail Y. et al., "Combined Injection of rAAV with Mannitol Enhances Gene Expression in the Rat Brain," Molecular Therapy 2001 vol. 3 No. 2 pp. 225-232 (8 pages).
Matalon, Reuben "Adeno-Associated Virus-Mediated Aspartoacylase Gene Transfer to the Brain of Knockout Mouse for Canavan Disease," Molecular Therapy vol. 7, No. 5, May 2003 pp. 580-587 (8 pages).
McCarty, D. M. et al., "Integration of Adeno-Associated Virus (AAV) and Recombinant AAV Vectors," Annu Rev Genet, 2004 vol. 38, pp. 819-845 (29 pages).
Muldoon, Leslie L. et al., "Comparison of Intracerebral Inoculation and Osmotic Blood-Brain Barrier Disruption for Delivery of Adenovirus, Herpesvirus, and Iron Oxide Particles to Normal Rat Brain," American Journal of Pathology, vol. 147, No. 6, Dec. 1995 pp. 1840-1851 (12 pages).
Murtha, Lucy A. et al., "Cerebrospinal fluid is drained primarily via the spinal canal and olfactory route in young and aged spontaneously hypertensive rats," Fluids and Barriers of the CNS 2014, 11:12 (9 pages).
Nilaver, Gajanan et al., "Delivery of herpesvirus and adenovirus to nude rat intracerebral tumors after osmotic blood-brain barrier disruption," Proc. Natl. Acad. Sci. USA vol. 92, pp. 9829-9833, Oct. 1995 (5 pages).
"Non-Final Office Action," for U.S. Appl. No. 15/891,879 dated Jun. 25, 2020 (29 pages).
Osmon, Karlaina J. et al., "Systemic Gene Transfer of a Hexosaminidase Variant Using an scAAV9.47 Vector Corrects Gm2 Gangliosidosis in Sandhoff Mice," Human Gene Therapy, vol. 27 No. 7 pp. 497-508 (11-13).
Passini, Marco A. et al., "Intraventricular Brain Injection of Adeno-Associated Virus Type 1 (AAV1) in Neonatal Mice Results in Complementary Patterns of Neuronal Transduction of AAV2 and Total Long-Term Correction of Storage Lesions in the Brains of B-Glucuronidase-Deficient Mice," Journal of Virology, Jun. 2003, vol. 77, No. 22 p. 7034-7040 (7 pages).
Passini, Marco A. et al., "Widespread Gene Delivery and Structure-Specific Patterns of Expression in the Brain after Intraventricular Injections of Neonatal Mice with an Adeno-Associated Virus Vector," Journal of Virology, Dec. 2001, p. 12382-12392 (11 pages).
Pennisi, Elizabeth "The CRISPR Craze," Science vol. 341, Aug. 23, 2013, pp. 833-836 (5 pages).
Pinder, George F. et al., "Essentials of multiphase flow and transport in porous media," Hoboken, N.J. Wiley 2008 (272 pages).
Pullen, R.G. et al., "Bulk flow of cerebrospinal fluid into brain in response to acute hyperosmolality," Am J Physiol, vol. 253, pp. F538-45, Sep. 1987 (8 pages).
Rapoport, S.I. "Osmotic opening of the blood-brain barrier: principles, mechanism, and therapeutic applications," Cell Mol Neurobiol, vol. 20, pp. 217-230, Apr. 2000 (14 pages).
"Response to Non-Final Office Action," for U.S. Appl. No. 15/891,879, filed Sep. 25, 2020 (15 pages).
Robinson, P.J. et al., "Size selectivity of blood-brain barrier permeability at various times after osmotic opening," Am J Physiol, vol. 253, pp. R459-66, Sep. 1987 (9 pages).
Rosenberg, G.A. et al., "Bulk flow of brain interstitial fluid under normal and hyperosmolar conditions," Am J Physiol, vol. 238, pp. F42-9, Jan. 1980 (8 pages).
Rudehill, A. et al., "Pharmacokinetics and effects of mannitol on hemodynamics, blood and cerebrospinal fluid electrolytes, and osmolality during intracranial surgery," Abstract only. J Neurosurg Anesthesiol, vol. 5, pp. 4-12, Jan. 1993 (1 page).

(56) References Cited

OTHER PUBLICATIONS

Rudehill, Anders et al., "Effects of mannitol on blood volume and central hemodynamics in patients undergoing cerebral aneurysm surgery," Anesth Analg, vol. 62, pp. 875-880, Oct. 1983 (6 pages).
Thorne, Rg et al., "Delivery of Neurotrophic Factors to the Central Nervous System," Pharmacokinetic Considerations 2001; 40(12): 907-946 (40 pages).
Thorne, Robert G. et al., "In vivo diffusion analysis with quantum dots and dextrans predicts the width of brain extracellular space," PNAS Apr. 2006, vol. 103, No. 14 pp. 5567-5572 (6 pages).
Vulchanova, Lucy et al., "Differential Adeno-associated virus mediated gene transfer to sensory neurons following intrathecal delivery by direct lumbar puncture," Molecular pain 2010, 6:31 (9 pages).
Watson, G. et al., "Intrathecal administration of AAV vectors for the treatment of lysosomal storage in the brains of MPS I mice," Gene Therapy (2006) 13, 917-925 (9 pages).
Weed, L.H. et al., "Pressure changes in the cerebro-spinal fluid following intravenous injection of solutions of various concentrations," Am J Physiology 1919 vol. 48, No. 4, pp. 512-530 (19 pages).
Weed, Lewis H. "Studies on Cerebro-Spinal Fluid No. IV: The dual source of Cerebro-Spinal Fluid," J. Med. Res. 1914, vol. 31, pp. 93-118 (31 pages).
Weinberg, Marc S. et al., "Adeno-associated virus (AAV) gene therapy for neurological disease," Neuropharmacology 69 (2013) 82-88 (7 pages).
Wolff, J. A. et al., "An early history of gene transfer and therapy," Human Gene Therapy 5:469-480 (1994) (12 pages).
Zhang, E. T. et al., "Interrelationships of the pia mater and the perivascular (Virchow-Robin) spaces in the human cerebrum," J Anat, vol. 170, pp. 111-123, Jun. 1990 (13 pages).
Zlokovic, Berislav V. et al., "Strategies to Circumvent Vascular Barriers of the Central Nervous System," Congress of Neurological Surgeons vol. 43(4), Oct. 1998, pp. 877-878 (2 pages).
"Final Office Action," for U.S. Appl. No. 15/891,879 dated Jan. 4, 2021 (31 pages).
Iliff, Jeffrey J et al., "A Paravascular Pathway Facilitates CSF Flow Through the Brain Parenchyma and the Clearance of Interstitial Solutes, Including Amyloid β," Science Translation Medicine Aug. 15, 2012 vol. 4, Issue 147. pp. 1-11 (13 pages).
"Non-Final Office Action," for U.S. Appl. No. 15/891,879 dated Feb. 4, 2022 (27 pages).
"Response to Final Office Action," for U.S. Appl. No. 15/891,879 filed Jul. 6, 2021 (13 pages).
Belov, Vasily, et al. "Large-Volume Intrathecal Administrations: Impact on CSF Pressure and Safety Implications," Frontiers in Neuroscience, Apr. 2021, vol. 15, Article 604197, pp. 1-16.
Johnson, Richard N., et al. "Intracranial Pressure regulation: A comparative Model of Cerebrospinal Fluid Systems," T.-I.-T. Journal of Life Sciences, 1978, vol. 8, 79-92.
Mann, J. Douglas, et al. "Regulation of Intracranial Pressure in Rate, Dog, and Man," American Neurological Association, 3: 156-165, 1978.
"Notice of Allowance," for U.S. Appl. No. 15/891,879 dated Sep. 1, 2022 (15 pages).
"Response to Non-Final Office Action," for U.S. Appl. No. 15/891,879, filed Jul. 5, 2022 (15 pages).

\* cited by examiner

SYSTEMS AND METHODS FOR ENHANCED DISTRIBUTION OF A BIOLOGIC AGENT WITHIN THE BRAIN AND SPINAL CORD

This application is a continuation-in-part application of prior U.S. patent application Ser. No. 15/891,879, filed Feb. 8, 2018, which claims the benefit of U.S. Provisional Application No. 62/456,281, filed Feb. 8, 2017; this application also claims the benefit of U.S. Provisional Application No. 62/802,611, filed Feb. 7, 2019; the contents of all of which are herein incorporated by reference.

FIELD

Aspects herein relate to systems and methods for delivery of biologic agents to the central nervous system and, more particularly, for enhanced distribution of therapeutic macromolecules and particles, including polynucleotides and proteins, genetic vectors, and cells, to the brain and spinal cord parenchyma.

BACKGROUND

The improved understanding of the genetic basis of many neurological diseases and advancements in biotechnology are leading to the development of new therapeutic agents including polynucleotides and polypeptides that are able to precisely target the underlying cause of disease. In addition, animal studies and initial clinical investigations have shown that in-vivo gene vector transfer with chronic expression of these therapeutic agents enables long-term amelioration of disease (Weinberg, Samulski et al. 2013, Hocquemiller, Giersch et al. 2016, Karumuthil-Melethil, Nagabhushan Kalburgi et al. 2016, Osmon, Woodley et al. 2016). Alternatively, ex-vivo gene therapy, involving the genetic modification of cells outside the body that are then being delivered to affected tissue within the patient, has also resulted in long term benefit in the treatment of disease (Cartier, Hacein-Bey-Abina et al. 2009). These polynucleotides, polypeptides, gene vectors, and altered biologic cells are generally classified as biologic agents. The particle sizes of these biologic macromolecules, vector capsids, and cells are significantly larger than traditional pharmaceutical medications. This larger particle size diminishes diffusion transport and membrane permeability characteristics of these agents within biological systems compared to the traditional small-molecule therapeutic agents.

SUMMARY

Aspects herein relate to systems and methods for delivery of biologic agents to the central nervous system. In various embodiments, a method of administering a therapeutic agent to the central nervous system (CNS) is included. The method can include injecting a therapeutic agent into a first cerebrospinal fluid (CSF) region of the subject. The method can further include establishing fluid communication between a fluid reservoir and a second cerebrospinal fluid (CSF) region of a subject, the fluid having a hydraulic pressure at or above an intracranial pressure. The method can further include infusing a hyperosmotic fluid systemically.

In some embodiments, a kit is included. The kit can include a first reservoir and a first fluid configured to be disposed within the first reservoir. The first fluid can be isotonic or hypotonic. The kit can further include an instrument for injecting a therapeutic agent into a first CSF space. The kit can further include a conduit for providing fluid communication between the first reservoir and a second CSF space. The kit can further include a second reservoir and a second fluid configured to be disposed within the second reservoir. The second fluid can be hyperosmotic.

In some embodiments, a system is included. The system can include a first reservoir and a first fluid disposed within the first reservoir. The first fluid is isotonic or hypotonic. The system can include a conduit for providing fluid communication between the first reservoir and a second CSF space. The system can also include a second reservoir and a second fluid disposed within the second reservoir. The second fluid can be hyperosmotic.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

Aspects herein can be more completely understood in consideration of the following detailed description of various embodiments in connection with the accompanying drawings, in which.

Figure 1:
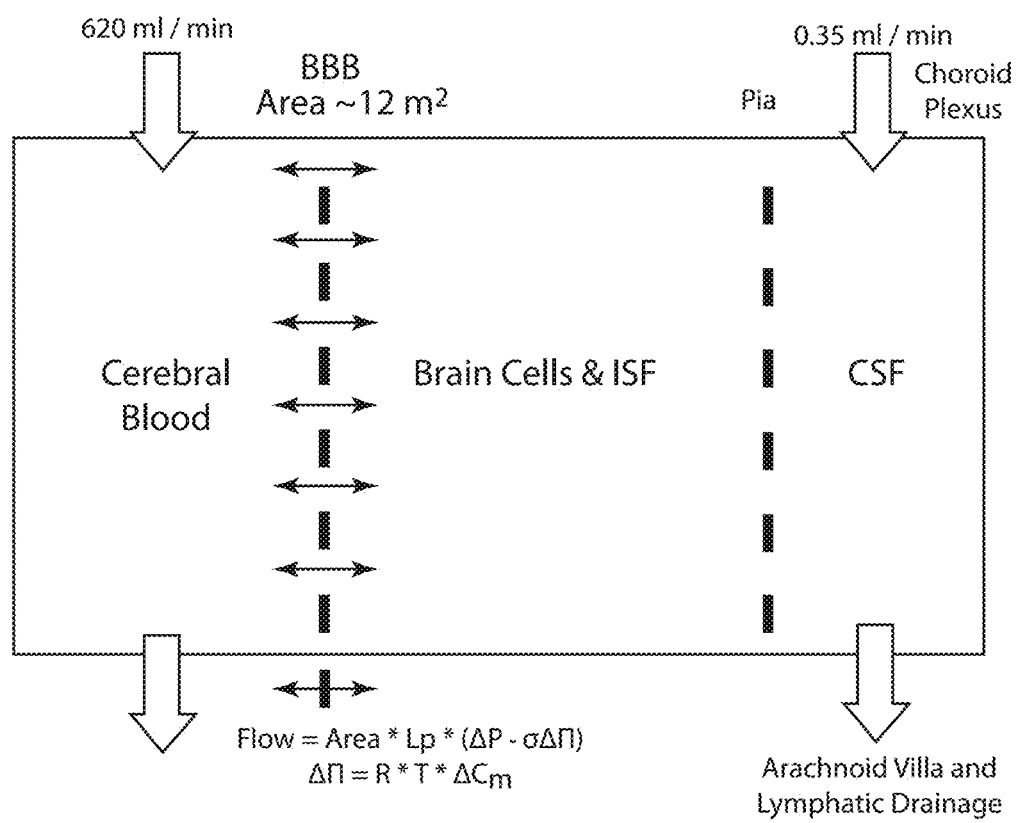
FIG. 1 is a simplified multi-compartment model of the CNS illustrating the Monro-Kellie hypothesis that the CNS has a fixed volume consisting of compartments of blood, parenchyma/ISF, and CSF.
Figure 2:
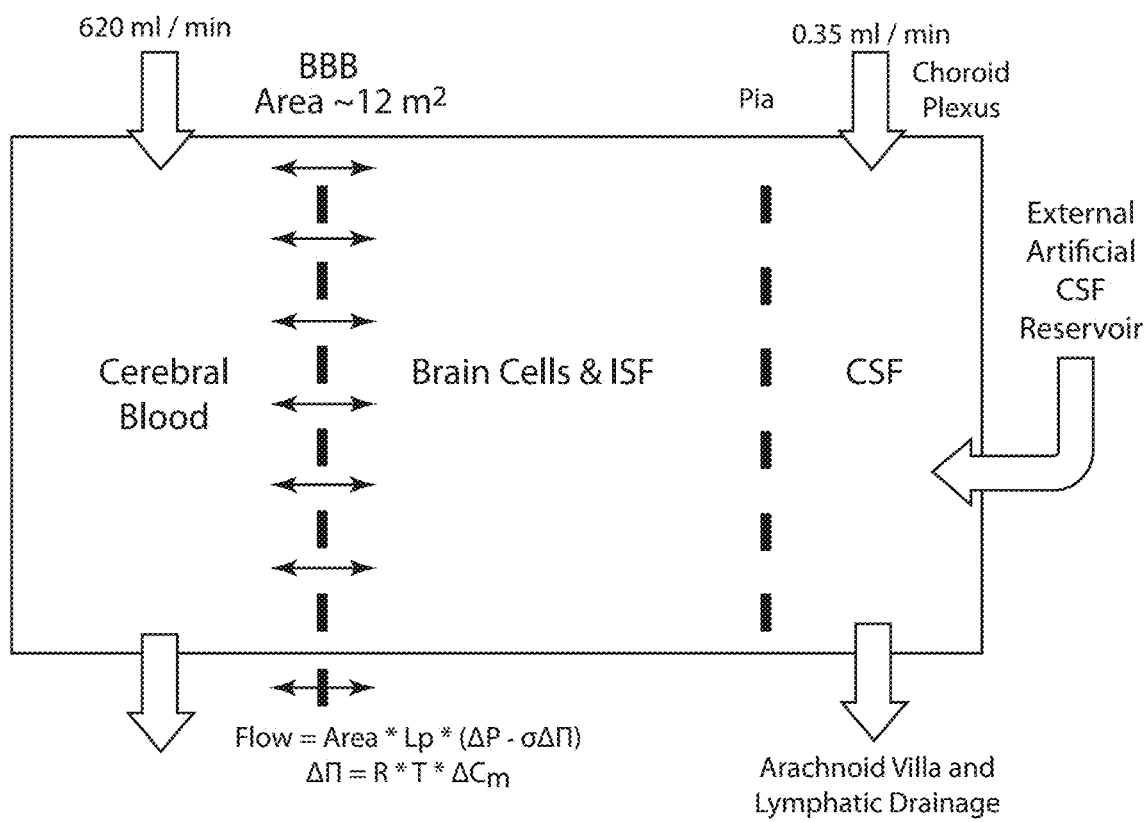
FIG. 2 is the same multi-compartment model of the CNS as shown in FIG. 1 with the addition of fluid flow connectivity from an external reservoir containing artificial CSF to the CSF compartment.

These drawings are to be considered general representations of some embodiments, and it will be appreciated that they are not drawn to encompass all embodiments, nor are they always drawn to scale. While aspects herein are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope of that described herein.

DETAILED DESCRIPTION

It is identified herein that there exists an unmet need for a simple, safe, and effective means of achieving broad distribution of polynucleotides, polypeptides, gene vectors, altered biologic cells and other large particle therapeutic agents throughout a human sized brain.

As described above, the particle sizes of biologic macromolecules, vector capsids, and cells are significantly larger than traditional pharmaceutical medications. This larger particle size diminishes diffusion transport and membrane permeability characteristics of these agents within biological systems compared to the traditional small-molecule therapeutic agents.

The large particle sizes of these agents thereby present additional restraints and limitations in adequately delivering these biologic agents for treating diseases, and in particular, diseases of the central nervous system (CNS).

While some diseases are primarily localized within particular regions of the CNS, as may be the case for Parkinson's disease, many diseases affect multiple regions, or in some cases, all regions of the CNS. Examples of diseases that have a diffuse effect within the CNS include cancers, such as advanced glioblastoma multiforme, and many neurodegenerative diseases, including Alzheimer's disease, Multiple Sclerosis, and many lysosomal storage diseases. The effectiveness of biologic agents is dependent on the delivery to the disease-affected cells. It is therefore believed that these diseases that broadly affect the CNS will require that a biologic agent reach a therapeutic concentration level within correspondingly broad regions of distribution in order to be effective.

Biologic agent transport characteristics are dependent on particle size. As is generally known by the Stokes-Einstein Equation, the diffusion coefficient decreases as the particle size increases. ($D=k_B T/6\pi\eta r$ where D is the diffusion coefficient, $k_B$ is Boltzmann's constant, T is the absolute temperature, $\eta$ is the dynamic viscosity, and r is the radius of an equivalent spherical particle.) The effective diffusion coefficient is further diminished by smaller size and greater tortuosity of extracellular tissue channels, such as those of dense brain tissue. With a smaller diffusion coefficient, diffusion becomes a less significant factor for transport of particles within a biologic system, and the particle distribution becomes increasingly dependent on convective flow. The relative significance of convection compared to diffusion for particle transport is quantified by the peclet number, $Pe=VL/De$, where L is the characteristic length, V the velocity, De the effective mass diffusion coefficient. Convection thereby also becomes relatively more important in the distribution of particles in large animals and humans that have a larger characteristic length compared to small animals, such as laboratory mice.

Classical pharmacokinetic (PK) theory models the distribution of small molecule pharmaceutical agents between body compartments. Classical PK theory assumes that the agents are well mixed within these compartments. The lack of significant diffusion mixing of large particle biologic agents precludes the fundamental application of classical pharmacokinetic theory within dense tissue, such as the brain. The distribution of biologic agents within the CNS is primarily govern by the flow of fluids surrounding and within the parenchyma and is better modeled by the physics of fluid flow, fluid physiology, and the convective particle transport within porous media.

The distribution of biologic agents into the CNS must also overcome physiologic barriers. The blood-brain barrier (BBB) separates the CNS from systemic blood circulation. This barrier is composed of a capillary endothelial layer and tightly associated accessory cells (pericytes, astrocytes). The BBB limits transport of large, hydrophilic molecules and cells from entering the CNS. The exception is for some specific proteins such as transferrin, lactoferrin and low-density lipoproteins, which are taken up by receptor-mediated endocytosis. Small molecule pharmaceutical agents depend on active or non-active transport across the BBB to reach the CNS, but the BBB is generally impervious to most biologic agents.

Multiple methods have been previously investigated for biologic agents to either overcome or bypass the BBB and enter the CNS, including: direct brain parenchyma injections, systemic intravenous delivery using unique particles or conjugates that aid transport across the BBB, systemic intravascular injections with accompanied BBB disruption, and injections into the cerebrospinal fluid compartments (intra-CSF).

Of particular interest is the use of in vivo gene therapy for potentially providing a durable long-lasting treatment or cure for neurodegenerative diseases affecting the CNS. AAV vectors have emerged as the favored carrier for CNS in-vivo gene transfer because of their effectiveness in transducing CNS cells; their ability to produce persistent, long-term expression of the transgene in CNS cells (Hadaczek, Eberling et al. 2010); and their inherent safety. Wild-type AAV is not known to cause disease even though a number of AAV serotypes frequently infect humans. In addition, the transgene delivered with AAV vectors does not predominately integrate into the host genome (McCarty, Young et al. 2004, FDA 2006). This not only reduces the potential of carcinogenesis, but also reduces potential issues that may be caused by the mutation of a host gene. The AAV capsid is the smallest of the viral vectors being used in gene transfer today. This small capsid diameter, approximate 20 to 25 nm, may permit greater mobility through the narrow extracellular spaces of the brain, which have been measured to be 38 to 64 nm (Thorne and Nicholson 2006). The use of AAV vectors therefore provides a number of advantages for in vivo gene delivery to the CNS, and yet, AAV, like other biologic agents, have limited transport across the BBB and require alternative methods for entering the CNS and being broadly distributed within the CNS tissue.

CNS Intraparenchymal Delivery

The concept of using a hydraulic pressure higher than that of the tissue in order to cause flow of the fluid containing the desired agent is termed convection enhanced delivery (CED), which has been described in U.S. Pat. No. 5,720,720 by Laske et al., entitled "CONVECTION-ENHANCED DRUG DELIVERY," which issued on Feb. 24, 1998. This convection of biologic agents may result in a greater volume of distribution than that possible with diffusion alone, but the volume of distribution is still limited by the size of the particle, the affinity of the particles to cells within tissue, and the general reduction in the flow rate inversely proportional to the square of the distance from the injection site. Thus, the volume of cells sufficiently transduced by an injection of AAV vector is limited to a small volume surrounding the injection site.

For example, without inducing damage to the tissue during the injection, the volume of cells sufficiently transduced surrounding each CED injection site resulting from CED injection of an AAV vector carrying genetic material has been shown to be less than one $cm^3$ (Bobo, Laske et al. 1994, Burger, Nguyen et al. 2005) (Axonal retrograde transport has also been shown to increase the distribution of AAV depending on the site of injection.) AAV intraparenchymal injections have been able to achieve transduction in regions throughout the small brain volume of mice (0.7 $cm^3$), but this method does not simply scale with brain size and results in the transduction of only a small percentage of the brain volume of larger animals and humans (approximately 1400 $cm^3$ for humans). Linninger et al. (2008) and others have developed computer models intended to optimize CED distribution (Linninger, Somayaji et al. 2008, Linninger, Somayaji et al. 2008), but these attempts to significantly increase the transduced volume by modifying the CED injection parameters have not been successful in increasing the volume of distribution from a single injection site. AAV particle distribution with CED is limited by narrow and tortuous pathways within dense CNS tissue, by the size of the AAV particles, and most importantly, by the tissue binding characteristics of the AAV serotype (Chen, Hoffer et al. 2005).

The majority of previously conducted AAV gene transfer clinical trials for CNS diseases have used stereotactic positioned, brain parenchyma injections of the gene vector in order to bypass the BBB (Hocquemiller, Giersch et al. 2016). For example, the first two gene transfer clinical studies used brain intraparenchymal CED injections of AAV vectors for Canavan disease and Batten disease (Janson, McPhee et al. 2002, Crystal, Sondhi et al. 2004). While the biochemical effectiveness was demonstrated in preclinical studies on murine models of these diseases, neither of these studies showed significant clinical improvement of the patients. It is believed that a primary cause for these results was the inadequate distribution of the gene vectors to all of the affected CNS regions (Nagabhushan Kalburgi, Khan et al. 2013). In attempts by others to overcome this limitation, clinical studies have used up to 12 brain injection sites, but the total percentage of CNS tissue transduced is still estimated to be less than one percent of the total human brain volume. Adding a sufficient number of brain injection sites to cause global transduction of a human CNS is not an acceptable option because of the associated surgical risks of intraparenchymal injections.

To increase the volume of transduced CNS tissue, a number of groups have explored the use of a hyperosmotic fluid infusion to overcome the limited vector distribution with intraparenchymal injections (Burger, Nguyen et al. 2005, Carty, Lee et al. 2010). Burger et al. utilized an intravenous (IV) injection of mannitol in conjunction with brain intraparenchymal delivery of the viral vector (Burger, Nguyen et al. 2005). The results showed a statistical increase in CNS transduction. Even with this enhancement, the AAV dispersion from each injection site averaged only 4 $mm^3$.

Systemic Gene Delivery Targeting the CNS

Prior to reports in 2009 by Foust et al. and by Duque et al., systemic delivery of viral vectors was not considered a viable means of transferring genes to the CNS because of the limited transport of vectors across the BBB. These groups reported that intravenous (IV) delivery of self-complementary AAV serotype 9 (scAAV9) in mice and cats resulted in brain cell transduction including astrocytes, glia, and neurons proximal to brain vasculature (Duque, Joussemet et al. 2009, Foust, Nurre et al. 2009). Studies in mice conducted by Gray et al. (2009) have verified these results in mice (Gray, McCown et al. 2009).

Intravenous hyperosmotic solutions have also been used to increase the permeability of the BBB and aid the transfer of systemically delivered drugs to the CNS (Rapoport 2000). Although AAV serotype 2 does not normally pass through the BBB, Fu et al. (2003) reported the transduction of a small number of brain cells when an IV injection of self-complementary AAV serotype 2 (scAAV2) was preceded by an IV injection of mannitol. While this resulted in transduction of some cells within the brain, the level of transduction was significantly less than what could be obtained by direct injections into the CNS (Fu, DiRosario et al. 2010). More recently, Louboutin et al. reported that a significant increase in sv40-derived viral vectors (approximately 45 nm diameter) entered the CNS when administered systemically in mice 20 minutes after a large intraperitoneal injection of mannitol (3 ml of sterile 25% mannitol in 0.9% saline per 100 g body weight, e.g., ~7 g/kg mannitol).

Even though these IV methods of AAV delivery have demonstrated broad distribution within the CNS of mice and may scale to the human size anatomy, it has not yet been established whether the low level of cell transduction within the CNS will be adequate for treatment of a neurodegenerative disease in man. Another major consideration for IV delivery of AAV is that the high AAV vector dose required with IV delivery in humans is projected to be expensive and potentially toxic.

As an alternative to intravenous systemic delivery, Janson et al. (2014) has reported on the delivery of single-stranded AAV5 vector directly to the carotid artery 60 seconds following a carotid artery injection of mannitol (~4 g/kg) (Janson, Romanova et al. 2014). Transgene expression occurred primarily on the ipsilateral side, and the procedure would need to be repeated on the contralateral side in order to achieve more global distribution. This BBB disruption method is similar to that first investigated by Stanley I. Rapoport (Rapoport 2000) and subsequently investigated for the delivery of gene vectors by others (Doran, Ren et al. 1995, Muldoon, Nilaver et al. 1995, Nilaver, Muldoon et al. 1995). While this localized delivery method has an advantage in both increasing the CNS uptake of the AAV vector and in reducing the required total dose for the AAV vector to sufficiently transduce cells within the CNS, it entails significantly more surgical risk than IV delivery of the hyperosmotic agent. Severe adverse events have been observed in clinical studies for the treatment of brain tumors using direct unilateral vertebral or carotid artery infusion with 25% mannitol at 5 to 12 mL/s for 30 seconds. These include non-reversible neurological damage (~1%) and seizures (~14%). One death was reported in a total of 630 procedures (Rapoport 2000).

Intra-CSF Gene Delivery

Prior studies using intraparenchymal CED have taken specific measures to avoid leakage of the therapeutic agents into the cerebrospinal fluid (CSF). It has been generally viewed that any therapeutic agent that leaks into the CSF will be "lost". On the other hand, while being less efficient, the delivery of AAV vectors into CSF using cerebroventricular, cisternal, or intrathecal spaces (intra-CSF) has been investigated in animal studies as a means of obtaining more global distribution. The results of these studies showed effective broad distribution in neonatal mice, while studies in older mice have resulted in low transduction efficiency generally limited to the ependymal tissue immediately adjacent to the CSF spaces (Davidson, Stein et al. 2000, Passini and Wolfe 2001, Fu, Muenzer et al. 2003, Passini, Watson et al. 2003, Broekman, Comer et al. 2006, Watson, Bastacky et al. 2006). Similarly, studies conducted by Keimel et al. (reviewed in U.S. Pat. No. 8,419,710) showed that even a large protein, alpha-L-iduronidase (71 kDa), which is smaller than an AAV capsid, continuously infused or injected by bolus into the cisterna *magna* of dogs primarily distributed to the superficial cerebral cortex and the cerebellum (Keimel, Passage et al. 2006, Keimel and Kaemmerer 2013, Kakkis U.S. Pat. No. 7,442,372). It has been suggested that the scattered and inconsistent transduction patterns using intra-CSF delivery are explained by the directional flow of brain interstitial fluid outward from the parenchyma and the limited diffusion of large particles to overcome this flow (Rosenberg, Kyner et al. 1980, Chen, Hoffer et al. 2005).

In 1999, Ghodsi et al., reported that transient systemic hyperosmolarity at the time of an intracerebroventricular (ICV) injection of an adenoviral vector would somewhat enhance the penetration of the vector across the ependymal cell layer in mice (Ghodsi, Stein et al. 1999). Similarly, in 2000, Leone et al. reported the experiences in rats and two patients of ICV injections of a non-viral lipid-entrapped, polycation-condensed delivery system (LPD), which were preceded by systemic mannitol (1 g/kg) intended to increase interstitial permeability (Leone, Janson et al. 2000). The authors qualitatively reported that the most intense transduction in the vicinity of the ependymal and subependymal cells in the ventricular spaces. Haiyan Fu et al., at the University of North Carolina, subsequently conducted a similar study that used AAV vectors delivered to the cisterna magna of mice. This study showed enhanced distribution of transduced cells when the AAV vectors were injected 20 minutes after an IV pre-treatment of 100 µL of 25% mannitol (approximately 1 g/kg body weight). This study illustrated the comparison of GFP expression with and without the pre-treatment of IV mannitol (Fu, Muenzer et al. 2003). More recent studies by this same group demonstrated that a single intracisternal injection of AAV vector with a pretreatment of IV mannitol had a significant neurological benefit in adult mucopolysaccharidosis IIIB mice (Fu, DiRosario et al. 2010). In gene transfer research using a single-stranded AAV vector injected into the cerebral ventricles of homozygous mucopolysaccharidosis type-1 mice, Janson et al. compared the transduction efficacy of the vector with systemic or ICV administration of mannitol. Both the systemic and the ICV co-administration of the mannitol with the ICV AAV injections were superior to the ICV AAV injections without co-injection of mannitol, which resulted mainly in expression within the choroid plexus and along the needle tract.

Methods have not previously been identified for the delivery and broad distribution of large particle biologic agents throughout the brain and spinal cord tissue of large animals and humans. Convective transport characteristics and the BBB permeability are major considerations in the development of these methods for large animals and humans. A simple, safe, and effective means of achieving broad distribution of biologic agents is needed to enable biologic agents to be effective in treating diffuse CNS diseases.

Brain Vasculature and the Blood Brain Barrier

The influence of systemic hyperosmotic agents on enhancing gene delivery requires an understanding of the anatomical aspects of the CNS vasculature and the role of the semipermeable membrane between the blood and the parenchyma interstitial fluid (ISF). The cranium blood macro- and micro-vessels together occupy a significant (25 to 30%) of the total brain volume with a surface area of approximately 12 square meters for humans (Zhang, Inman et al. 1990). With every brain cell located within 20 m of a capillary, delivery across the walls of these vessels is a logical means of globally transferring a drug agent throughout the CNS. But as described above, the blood vessels within the brain are composed of tight-junctioned endothelial cells and are further surrounded by a thin basal lamina that combine to form the blood-brain barrier (BBB). The vessel walls also contain contractile pericyte cells that serve to control blood flow through the vessels. Closely spaced astrocyte end feet further surround the intracerebral blood vessels. The endothelial cell tight junctions have been shown to contain a number of proteins, including membrane-spanning glycoproteins called cadherins, which limit paracellular transport (Rapoport 2000). Under normal conditions, the passage of drugs through the BBB has been shown to be directly related to lipid solubility (octanol-water partition coefficient, Log $P_{octanol}$) (Habgood and Ek 2010).

Interstitial Fluid

The brain is a dense tissue and this further limits the distribution of large particles within the parenchyma. The brain parenchyma extracellular space has been estimated to have a normal width of 38 to 64 nm (Thorne and Nicholson 2006). The size of this extracellular space and the tortuosity of the grey matter cell structure restrict diffusion and can also restrict the convective movement of particles as the size of the particles approach the size of the extracellular space. The particle outer dimensions are therefore a factor for both the diffusion and the convection within the brain.

The surface area of cerebral capillary endothelium is approximately 100 cm$^2$ per gram of brain tissue (Zhang, Inman et al. 1990), and this large surface area, even with its tight junctions, accounts for substantial fluid seepage into the brain. This flow across the BBB, plus the water created by the glycolysis of glucose within brain cells, is the source of interstitial fluid (ISF). A portion of this ISF drains into the CSF compartments.

Figure 3:
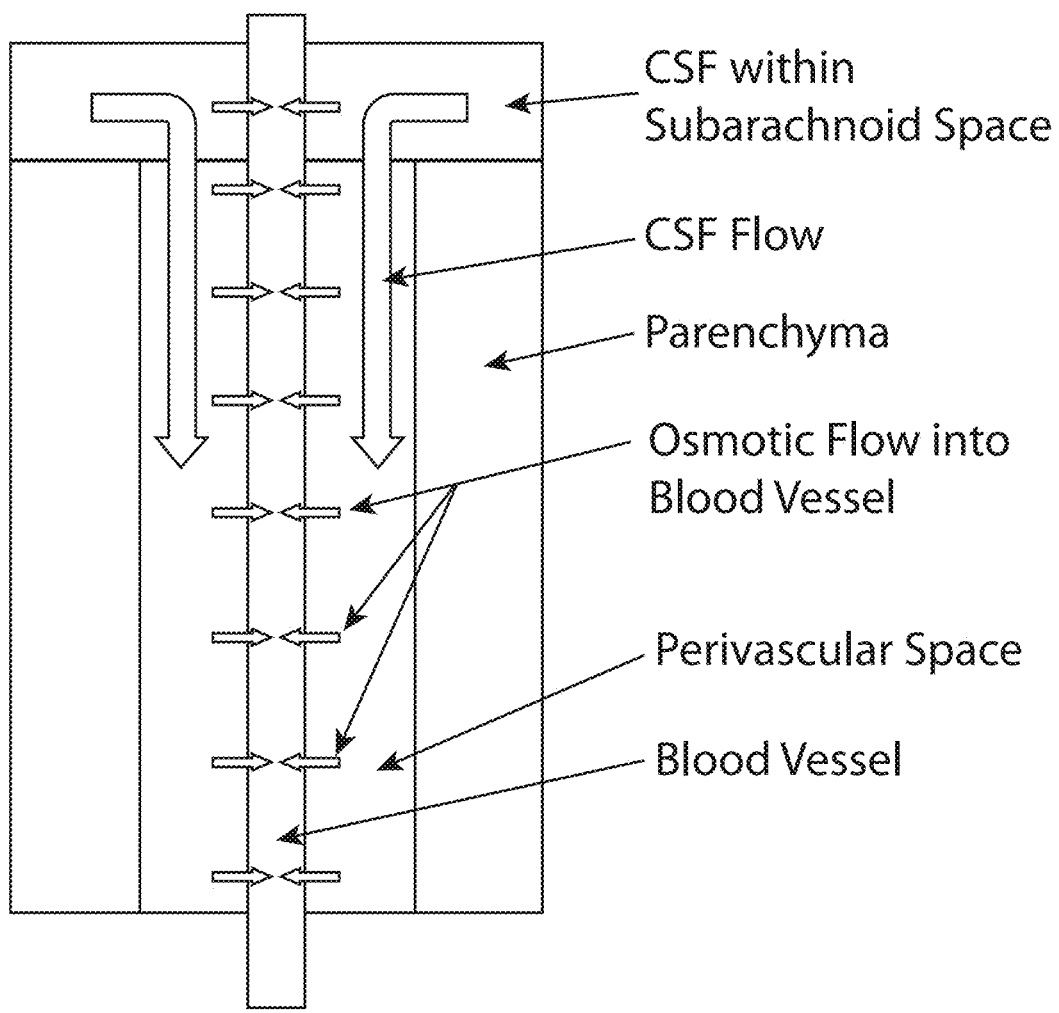
FIG. 3 is an illustration of perivascular spaces that emanate from the brain surface and provide a route of fluid flow from the CSF compartment to deep brain regions.

Perivascular spaces, as illustrated in FIG. 3, surround both veins and arteries from the subarachnoid spaces down to the level of arterioles and venules, but not down to the capillaries (Pullen, DePasquale et al. 1987). The ISF normally drains from the brain to the CSF through a network of fluid channels, which include these perivascular spaces. These brain extracellular spaces are in fluid contact with the CSF through porous openings in the pia layer. Large protein molecules readily cross the pia. In general, the flow of a fluid through the porous brain parenchyma can be modeled by Darcy's law: v=K∇p, where v is the fluid velocity vector, K is the hydrostatic conductivity tensor, and ∇p is the hydrostatic pressure gradient; but, a more detailed analysis may be required to account for the perivascular fluid channels.

Cerebral Spinal Fluid

CSF is a product of both the secretion of the ventricular choroid plexus and the ISF drainage from the parenchyma tissue, as noted above (Weed 1914, Pullen, DePasquale et al. 1987). It has been estimated that two thirds of the total CSF is secreted by the choroid plexuses (Johanson, Duncan et al. 2008). The ISF secretion rate at the BBB is substantially slower ($\frac{1}{100}$ when normalized for surface area) than the CSF secretion from the choroid plexus, but because of the large BBB surface area, a significant percentage of CSF originates from the ISF. The CSF drains out of the CNS into both the blood through the arachnoid villa and into the lymph along the cranial nerves and the spinal nerve root ganglia. A large percentage of protein injected into CSF has been shown to pass into the lymph (Cserr and Knopf 1992).

CSF Flow in Response to Hydrostatic Pressure

An oscillatory movement of CSF occurs in response to pulsatile cardiac pressure (Greitz 1993). With cardiac systole, intracranial blood vessels expand, and CSF is forced out of the ventricles and cranial subarachnoid spaces and moves into a compliant portion of the lower spinal intrathecal space. This CSF flow is then reversed during diastole. By itself, this oscillatory movement does not result in net flow of CSF, but does provide limited CSF mixing. With this, the fourth ventricle and the cisterna magna, in particular, serve as CSF mixing chambers (Enzmann and Pelc 1991).

Normally, the average CSF hydrostatic pressure is equal to the cerebral venous pressure minus the elastic forces of the venous walls. The response to mechanically induced, incremental changes in the CSF hydrostatic pressure was investigated by Noell and Schneider (Davson and Segal 1996). They found that incrementally raising the cisternal hydrostatic pressure resulted in a corresponding increase in intracranial venous pressure. This is as one would expect. Gradually raising the intracranial pressure (ICP) above that of the blood vessels will cause a collapsing force on the vessels, but the vis a tergo of the arterial blood will in-turn cause the capillary pressure to rise thereby preventing vessel collapse and maintaining blood flow. It has also been shown by Harvey Cushing in 1902 that as the CSF hydrostatic pressure is raised above the arterial systolic blood pressure, an autoregulatory response occurs, now known as the Cushing Reflex, that elevates the blood pressure and maintains blood flow to the brain (Cushing 1902). Therefore, not even large induced increases in the ICP will result in a steady state pressure gradient across the BBB.

The drainage (absorption) of CSF into both the arachnoid villa and lymphatic pathways has been shown to be linearly related to ICP (Cutler, Page et al. 1968, Boulton, Armstrong et al. 1998). This relationship is termed the resistance to absorption. Increasing ICP will cause a corresponding increase in bulk CSF flow towards the arachnoid villa and areas of lymphatic drainage.

Osmotic Flow Across the Blood-Brain Barrier

As noted above, a systemic infusion of a hyperosmotic solution has been shown to increases the CNS distribution of intra-CSF and IV delivered viral vector particles. The intra-CSF delivery methods may benefit from brain ISF flow arising from osmotic 'water' flow across the BBB. On the other hand, a systemically delivered vector may also require a sufficient disruption in the BBB to enhance passage of viral capsids into the brain.

Systemic delivery of a hyperosmotic solution is known to have an effect on the bulk flow of ISF. Rosenberg et al. studied the normal flow rate of ISF and the flow after systemic infusion of mannitol in both gray and white matter of cats. Under normal conditions, ISF flow was negligible in gray matter, but the ISF flowed toward the ventricles at a rate of 10.5 µm/min in white matter. Four hours following the start of a 30 minute IV infusion of 20% mannitol (1.5 to 3 g/kg), the bulk flow of ISF in gray matter changed direction away from the ventricles (Rosenberg, Kyner et al. 1980).

The brain vasculature can be considered a semipermeable membrane due to the restrictions imposed by its tight-junctioned endothelial cells. The Starling equation relates the flow across a semipermeable membrane to the hydrostatic pressure and osmotic pressure differences across the membrane:

$$f = A\, Lp(\Delta P - \sigma \Delta \Pi)$$

where f is the flow across the membrane, A is the membrane area, Lp is the hydrostatic or filtration coefficient, $\Delta P$ is the hydrostatic pressure across the membrane, $\sigma$ is the reflection coefficient, and $\Delta \Pi$ is the osmotic pressure. The osmotic pressure can be further modeled using van't Hoff's law:

$$\Delta \Pi = RT\Delta C$$

where R is the gas constant, T is the absolute temperature, and $\Delta C$ is the combined osmolarity difference of solutes across the membrane (Osm/L). Under normal conditions, the osmolality of the human cerebrospinal fluid is between 280 and 300 mOsm/kg of $H_2O$. Osmolarity is the amount of the total osmoles of all solute per liter of solution, whereas osmolality (with an "1") is the measure of the total osmoles of all solutes per kilogram of solvent. Blood typically has an osmolality between 275 and 295 mOsm/kg. The normal intracranial pressure (ICP) is 5 to 15 mmHg (or 7 to 20 cmH$_2$O). An equivalent intracerebral venous pressure must counter this ICP in order to maintain patency of the vessels. The cranium and spinal column space can be simplistically modeled, as shown in FIG. 1.

When the osmolarity of the intracranial blood is increased, an osmotic pressure develops across the BBB. As reflected in Starling's equation, this results in a net flow, primarily water, through the BBB into the blood. If this flow is greater than the CSF synthesis rate, the total volume of ISF and CSF will decrease. This, in turn, will increase the solute concentration of the ISF and CSF and also reduce the intracranial pressure. Both of these factors will offset the initial osmotic force for flow across the BBB. Also to be considered is the Monro-Kellie hypothesis that states that the cranium has a fixed volume and that the total volume of brain parenchyma, the CSF, and the cerebral blood must remain nearly constant. Therefore, a reduction in the volume of ISF and CSF must be, at least transiently, offset by an increase in the cranial blood volume. Volume homeostasis will eventually return by either BBB backflow from the cerebral capillaries or by CSF synthesis.

Methods and Systems

In consideration of the preceding points, embodiments herein can include a method of administering a therapeutic agent to the central nervous system (CNS) including steps of injecting a therapeutic agent into a first cerebrospinal fluid (CSF) region of the subject, establishing fluid communication between a fluid reservoir and a second cerebrospinal fluid (CSF) region of a subject and infusing a hyperosmotic fluid systemically.

The hyperosmotic fluid causes an osmotic pressure across the BBB, resulting in a net flow of fluid outward across the BBB. This fluid flow can, in turn, cause the therapeutic agent to be transported from the injection site in a CSF region into the parenchyma and ISF thereof through convection. The fluid reservoir, in fluid communication with a CSF region, can serve as a source of fluid and be drawn into the CSF region in order to replace the volume of fluid carrying the therapeutic agent and moving from the CSF region and into the parenchyma and ISF thereof.

As such, the fluid coming from the fluid reservoir prevents the pressure within the CSF region from dropping to a level that would inhibit further movement of fluid from the CSF region and into the parenchyma and ISF thereof. This is because in the absence of fluid being drawn in from the fluid reservoir, osmotic induced flow across the BBB reduces ISF volume, but with a low CSF synthesis rate and keeping with the Monro-Kellie Hypothesis, the volume of cerebral blood would have to increase so that the total CNS volume remains constant. This expansion of the volume of cerebral blood would happen at least partially in lieu of further fluid movement across the BBB and thus would inhibit further convection of the therapeutic agent.

The method can specifically include injecting a therapeutic agent into a first cerebrospinal fluid (CSF) region of the subject. It will be appreciated that the injection can be accomplished in various ways. In some embodiments a cannula or needle can be used to inject the therapeutic agent.

In some embodiments, the method can include establishing fluid communication between a fluid reservoir and a second cerebrospinal fluid (CSF) region of a subject. It will be appreciated that fluid communication can be established in various ways and using various pieces of equipment. In various embodiments, the fluid having a hydraulic pressure at or above an intracranial pressure. In some embodiments, the method can further include inserting a conduit to provide fluid communication between the reservoir and the second CSF region of the subject. In some embodiments, the method can further include infusing a hyperosmotic fluid systemically.

The various steps of methods herein can be performed in various specific orders. In some embodiments, the step of injecting the therapeutic agent into the first cerebrospinal fluid (CSF) region of the subject is performed before, during or after the step of infusing the hyperosmotic fluid systemically. In some embodiments, the step of injecting the therapeutic agent into the first cerebrospinal fluid (CSF) region of the subject is performed before the step of infusing the hyperosmotic fluid systemically. In some embodiments, the gap in time between injecting the therapeutic agent and beginning infusion of the hyperosmotic fluid systemically (regardless of which comes first) can be approximately 0 seconds, 0 to 30 seconds, 30 to 60 seconds, 1 minute to 2 minutes, 2 minutes to 3 minutes, 3 minutes to 4 minutes, 4 minutes to 6 minutes, 6 minutes to 10 minutes, 10 minutes to 15 minutes, or 15 minutes to 20 minutes or more.

Figure 4:
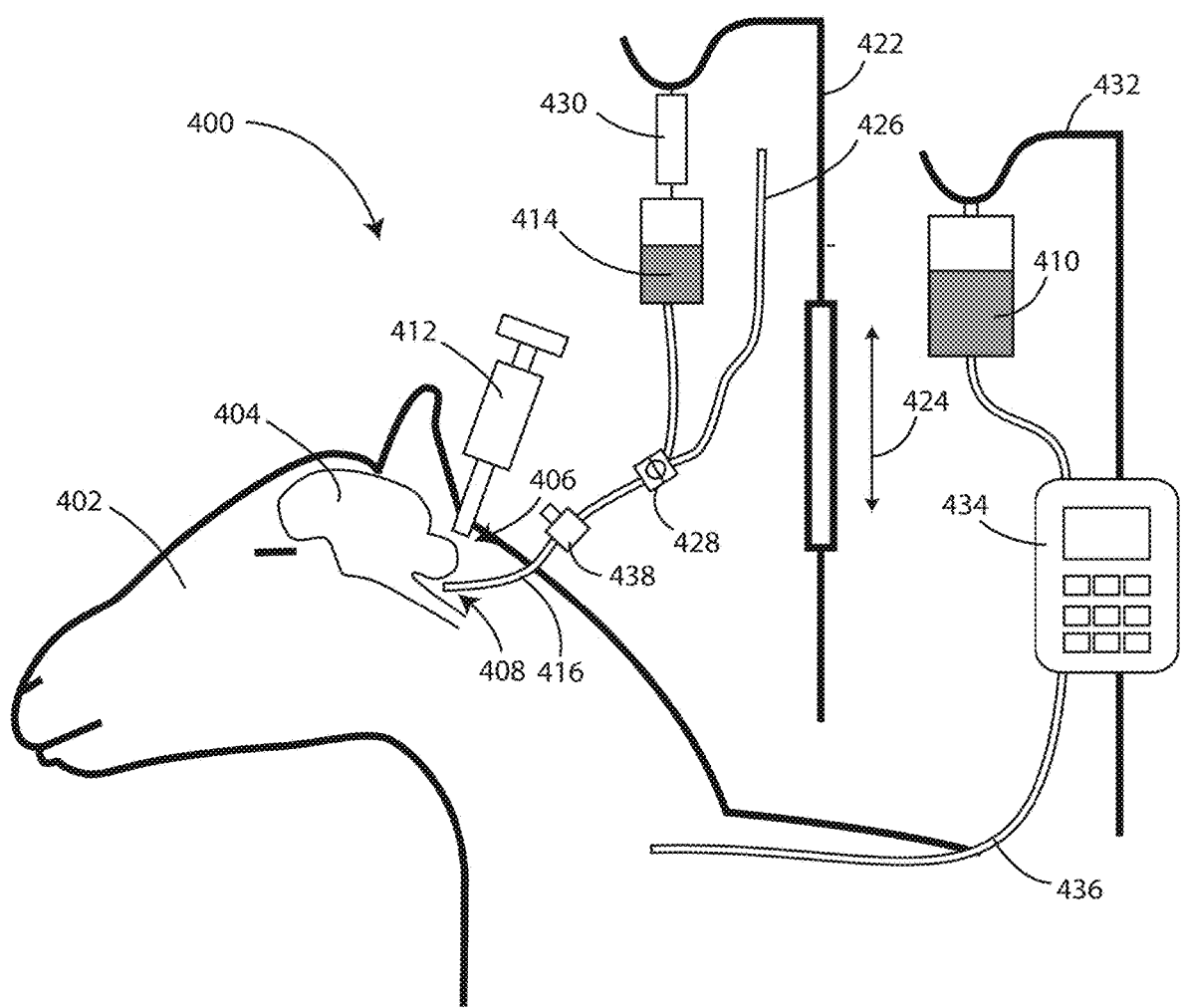
FIG. 4 is a schematic diagram of a system in accordance with various embodiments herein.
Figure 5A:
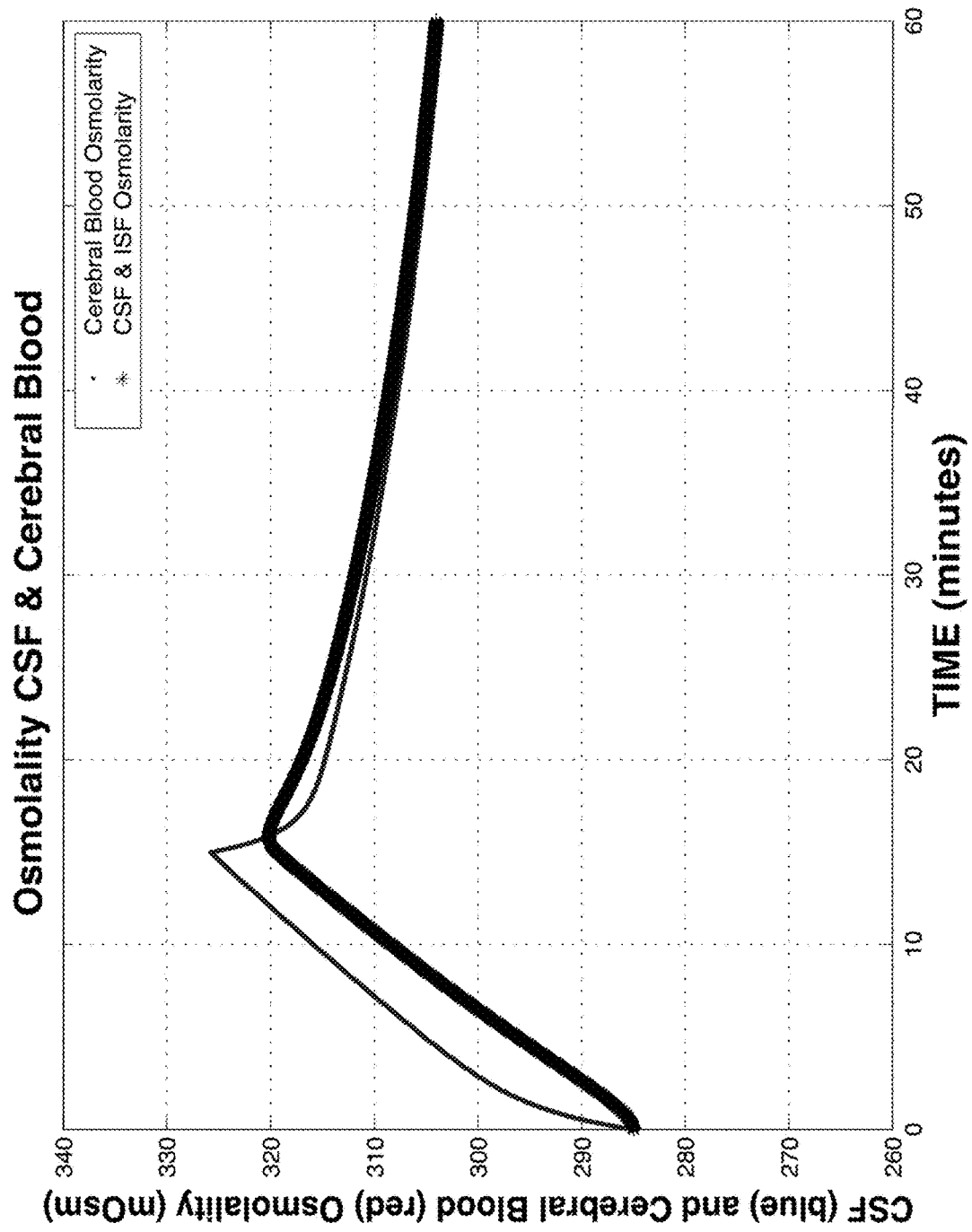
FIGS. 5A-5D include graphs generated from computer simulations of computer simulations of the multi-compartment model during the intravenous delivery of 20% mannitol (1 g/kg) for 15 minutes: (A) Osmolality of CSF and cerebral blood without fluid connectivity to the artificial CSF reservoir, as shown in FIG. 1; (B) Osmolality of CSF and cerebral blood with fluid connectivity to the artificial CSF reservoir, as shown in FIG. 2; (C) Fluid flow into the brain across the BBB without fluid connectivity to the artificial CSF reservoir, as shown in FIG. 1; (D) Fluid flow into the brain across the BBB with fluid connectivity to the artificial CSF reservoir, as shown in FIG. 2.
Figure 5B:
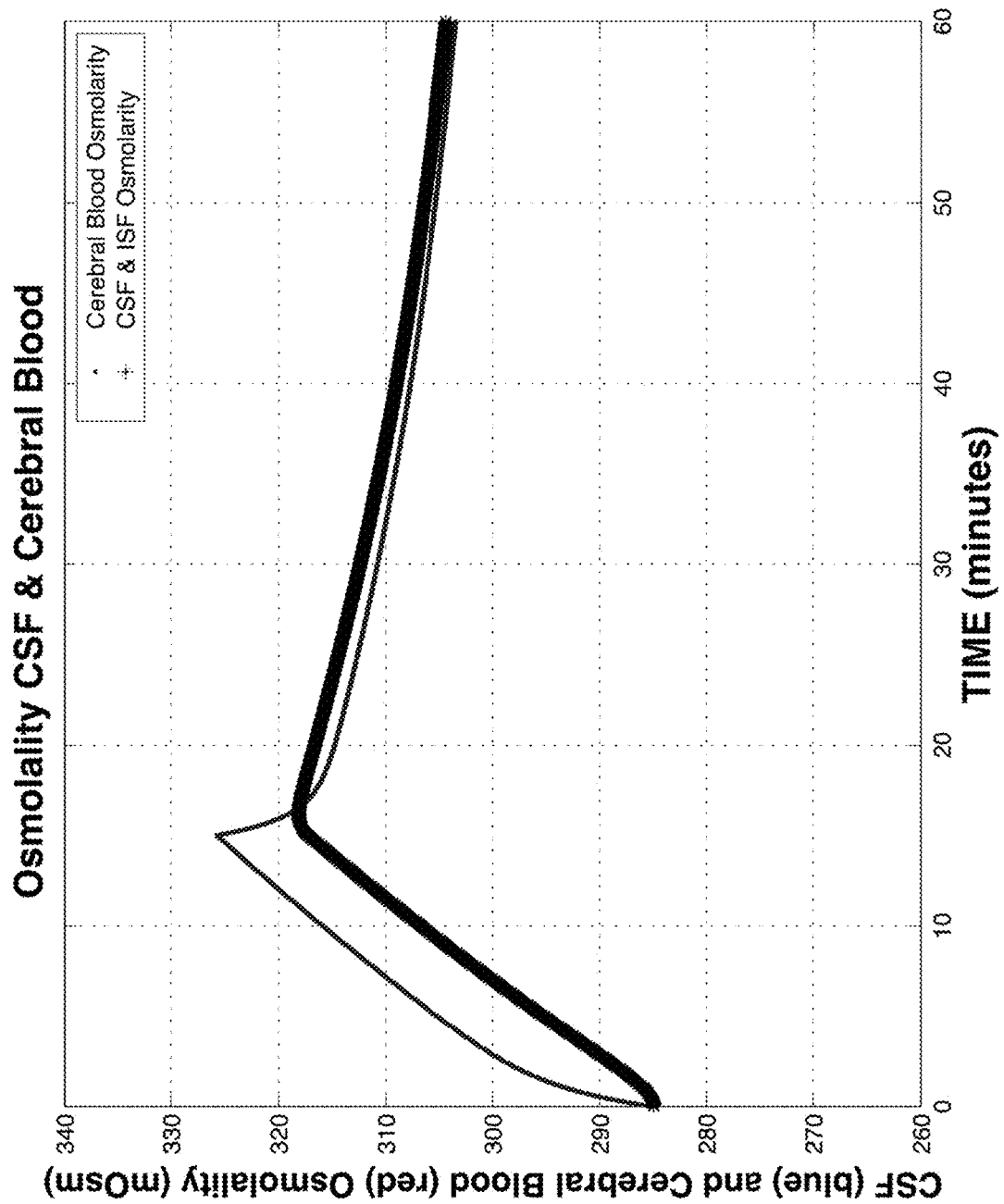
Figure 5C:
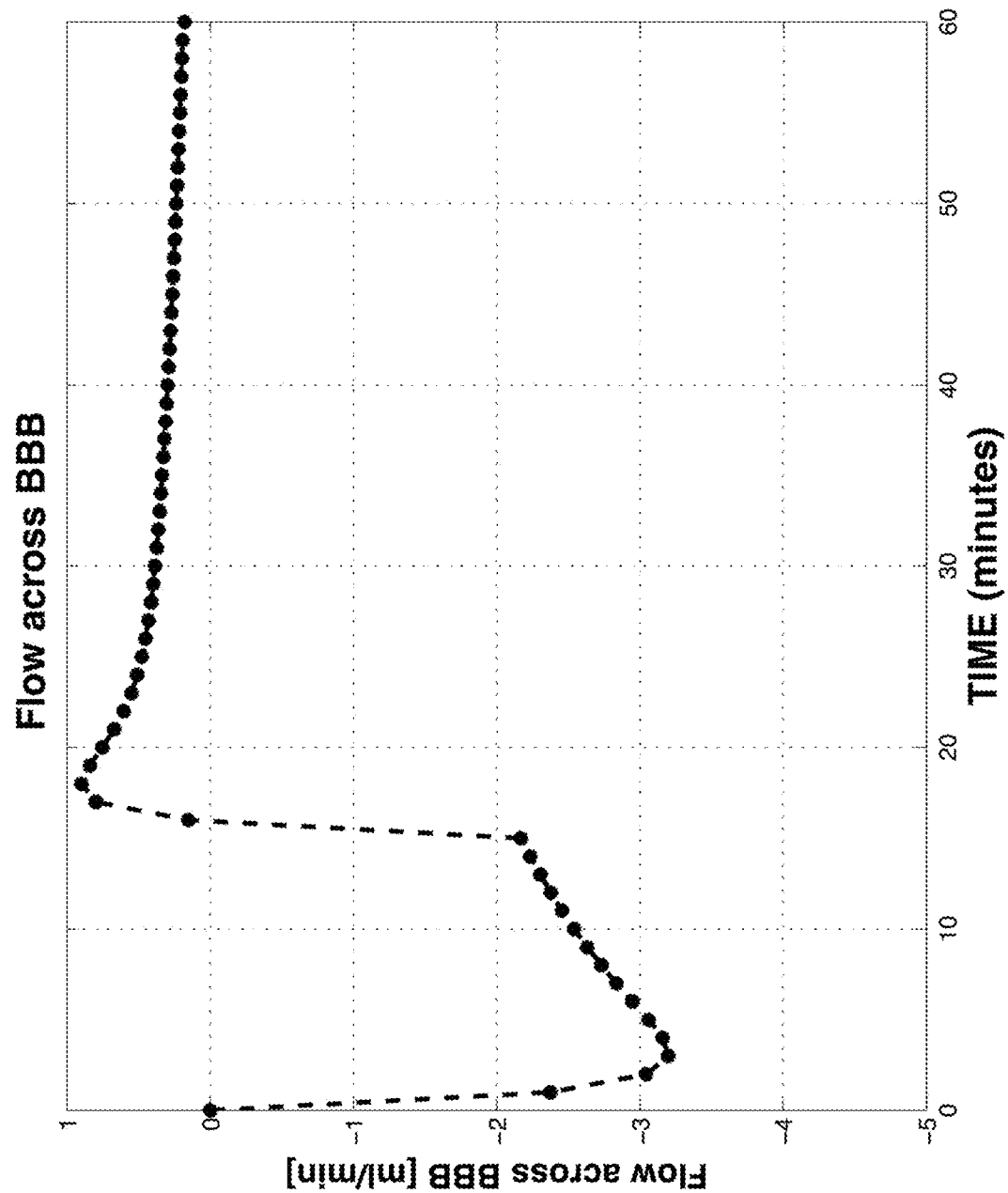
Figure 5D:
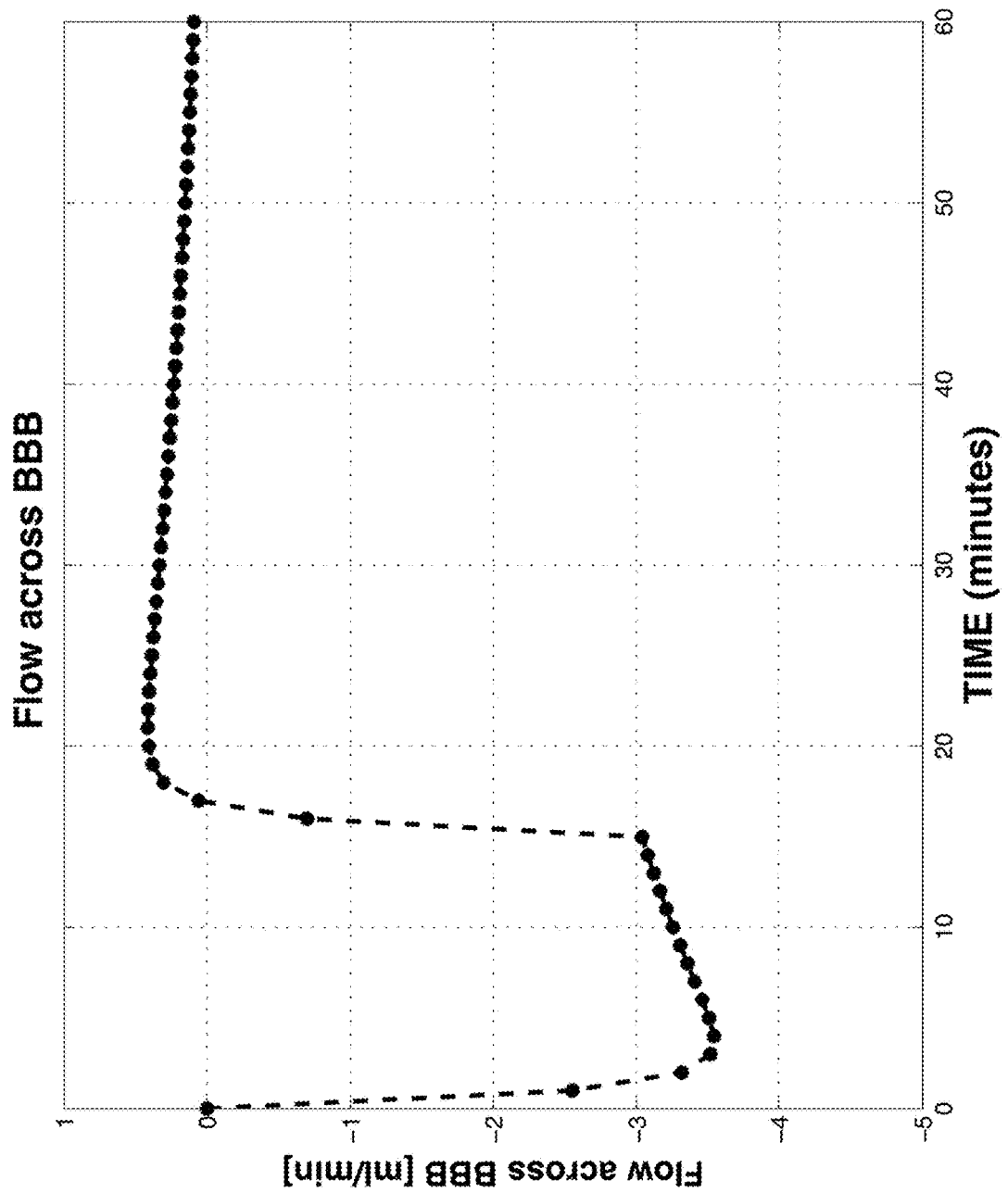
Figure 6A:
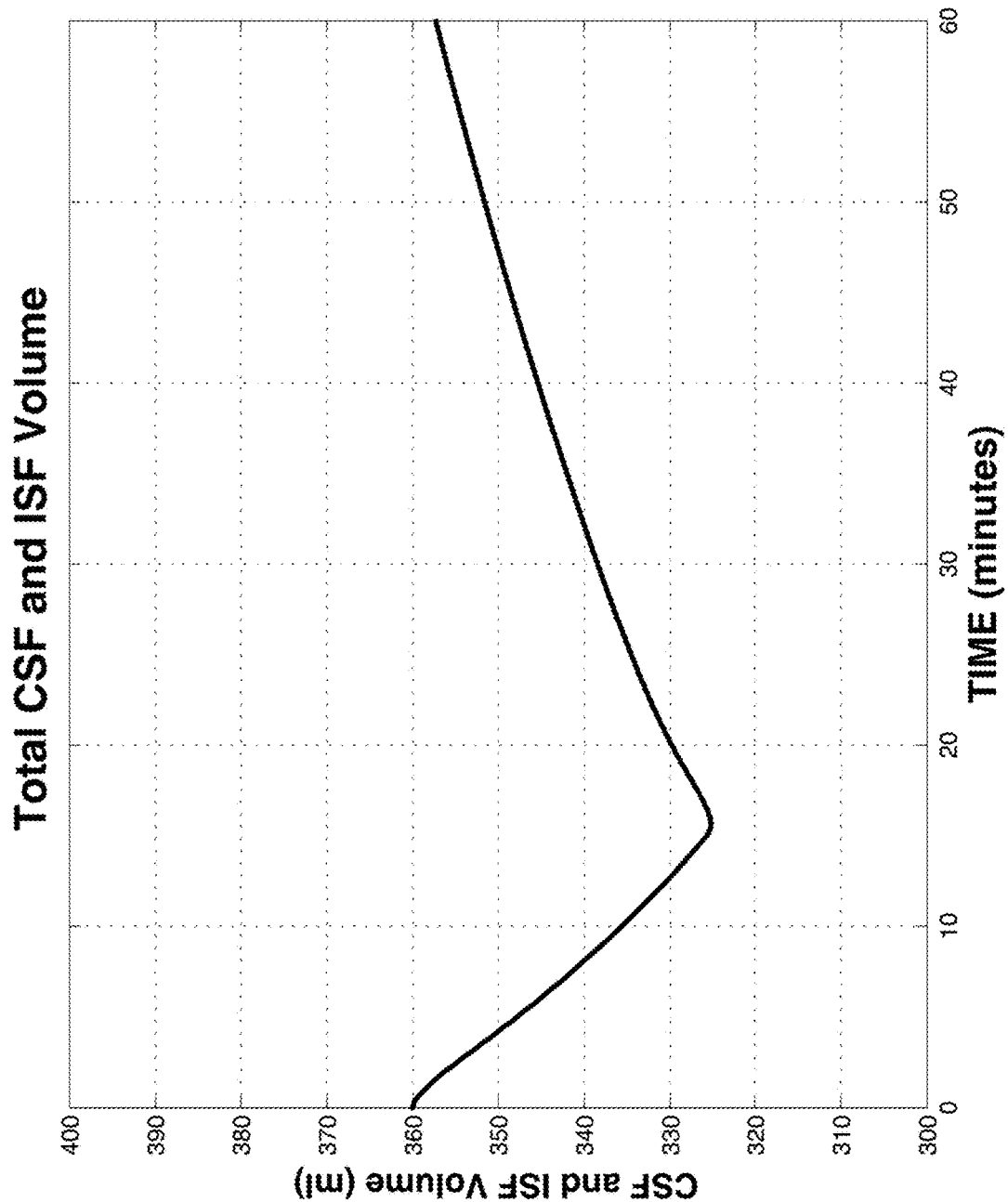
FIGS. 6A-6C include graphs generated from computer simulations of computer simulations of the multi-compartment model during the intravenous delivery of 20% mannitol (1 g/kg) for 15 minutes: (A) Total combined ISF and CSF volume without fluid connectivity to the artificial CSF reservoir, as shown in FIG. 1; (B) Total combined ISF and CSF volume with fluid connectivity to the artificial CSF reservoir, as shown in FIG. 2; (C) Reservoir volume change and cumulative fluid volume crossing the BBB with fluid connectivity to the artificial CSF reservoir, as shown in FIG. 2.
Figure 6B:
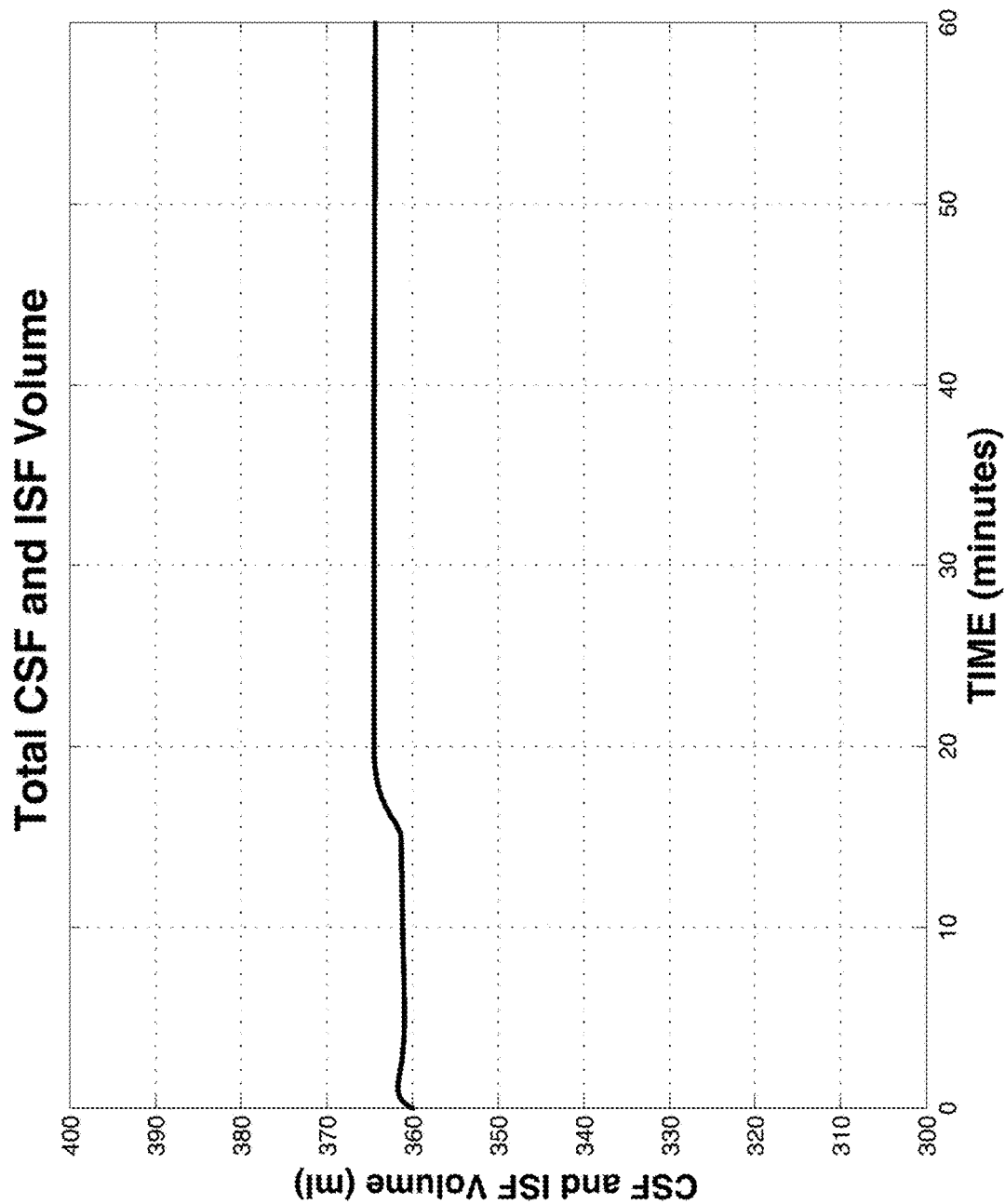
Figure 6C:
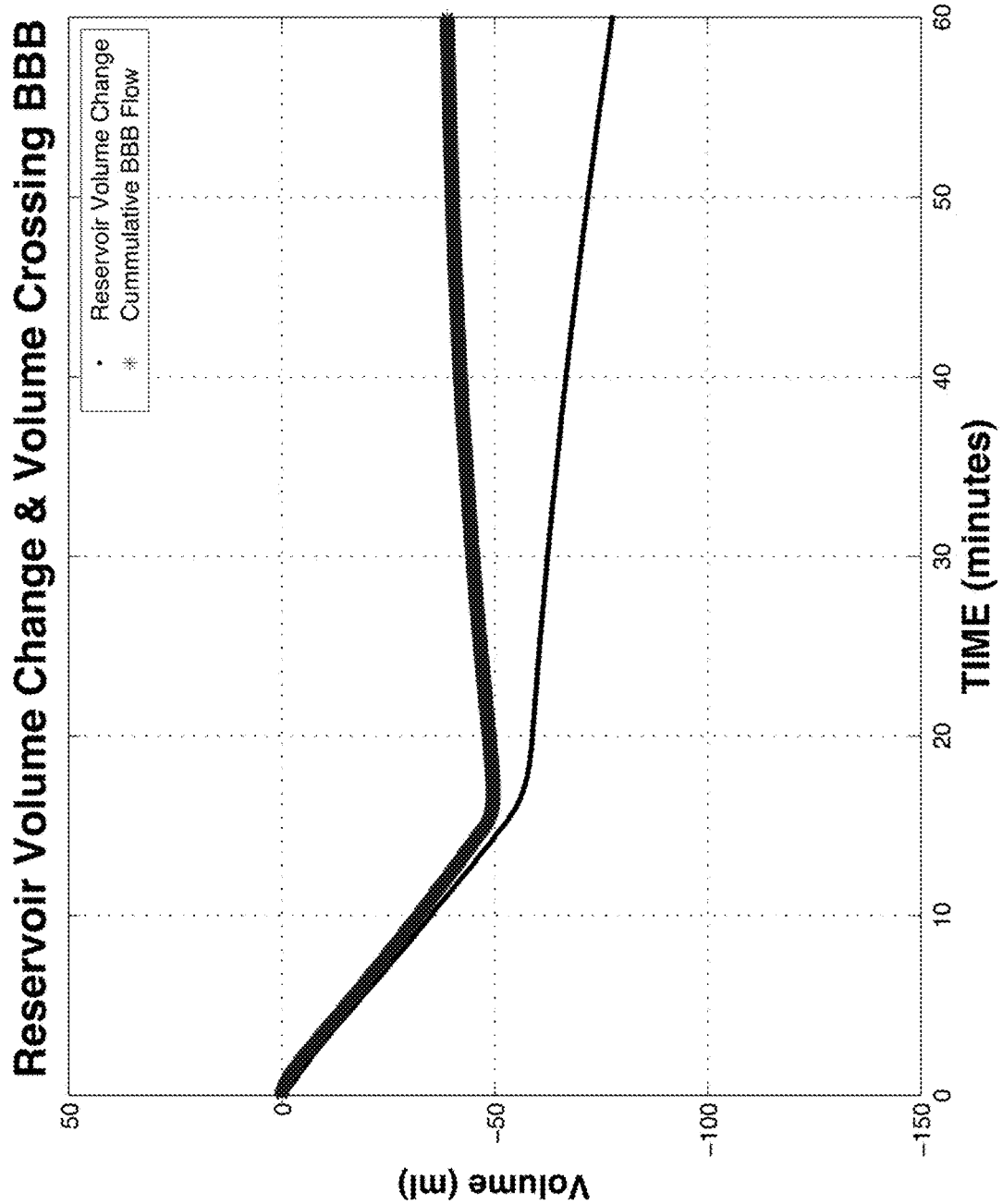

Referring now to FIG. 4, a schematic diagram of a system 400 in accordance with various embodiments herein. The system 400 can include components for the execution of various steps in accordance with methods herein. The system 400 can be effective to administer a therapeutic agent to the central nervous system (CNS) of a subject 402. While the subject 402 shown in FIG. 4 is non-human, it will be appreciated that in various embodiments the subject can be a human. The subject 402 can include a CNS 404. The subject 402 can include a first CSF space 406 and a second CSF space 408.

The system 400 can further include an instrument 412 to deliver or inject an active agent, such as a syringe or similar instrument, to a first CSF space 406.

The system 400 can further include a reservoir 414 including an isotonic or hypotonic liquid, including but not limited to, a synthetic or artificial cerebrospinal fluid. The reservoir 414 can be in fluid communication with a second CSF space 408 via a conduit 416. The conduit 416 can provide a sterile means of transporting the fluid from the reservoir 414 to the second CSF space 408. As used herein, the term hypotonic shall be interpreted the same as hypoosmotic, the term hypertonic shall be interpreted the same as hyperosmotic, and the term isotonic shall be interpreted the same as isosmotic, unless the context dictates otherwise.

In some embodiments, a measurement device 426 for measuring pressure can be included. For example, the measurement device 426 can be a liquid column manometer. However, other devices for measuring pressure are contemplated herein. With use of a liquid column manometer, the height of the fluid in the CSF reservoir 414 can be adjusted to be at or above the height of the fluid in the manometer. It will be appreciated that the measurement device 426 could also take alternative forms, such as a pressure gauge.

A stopcock 428 (such as a three-way stopcock) can be included to selectively block or provide fluid communication with any of the inputs thereto (e.g., the device 426 for measuring pressure and the reservoir 414) and the output therefrom (e.g., conduit 416). For example, the stopcock can be actuated to selectively provide fluid communication between the device 426 for measuring pressure and the conduit 416 and second CSF space 408, while temporarily blocking fluid communication with the reservoir 414. This can allow for the specific measurement of pressure in the area of the second CSF space 408.

In some embodiments, a load cell 430 (or other type of device capable of measuring or being responsive to changes in weight) can be used to monitor the amount of fluid and/or the change in the amount of fluid in the reservoir 414. In some embodiments the load cell 430 can provide a read-out to recording equipment so as to document the rate and total fluid amount entering the CSF. In some embodiments, data from the load cell 430 can also be used to provide an indication as to when the procedure is complete. As merely one illustrative example, one could decide that sufficient convection of the therapeutic agent has occurred when 50 cc of CSF fluid from the reservoir has entered the CNS (wherein a one gram change in the CSF fluid weight is approximately equal to one cc of fluid entering the CNS.)

In some embodiments, an alternative access port 438 can be included. The alternative access port 438 can be used for injections and, in some cases, can be used for the injection of a therapeutic agent, such as those described herein.

The reservoir 414 can be suspended from (or otherwise attached to) an adjustable shepherd hook stand 422. The height of the adjustable shepherd hook stand 422 can be adjusted as shown by arrow 424. Adjusting the height of the adjustable shepherd hook stand 422 can allow for adjustment of the pressure of the fluid in the reservoir 414.

In various embodiments, the conduit 416 can be an intrathecal catheter or can at least include components of the same. In various embodiments, the conduit 416 can include tubing material such as polyvinylchloride (PVC), polyethylene, polyurethane, polyamide, silicone, synthetic rubber, and the like. An exemplary intrathecal catheter is described in US Publ. Appl. No. 2008/0140008, the content of which is herein incorporated by reference. In various embodiments, the conduit can include a cannula. The interior diameter of the conduit can be sufficiently large so as to avoid creating a relatively large pressure drop between the reservoir and the end of the conduit 416 where it provides fluid communication with the second CSF space 408.

The system 400 can include a reservoir 410 including a hyperosmotic liquid to be infused systemically to the subject 402. Details of exemplary hyperosmotic liquids are described in greater detail below. The reservoir 410 for the hyperosmotic liquid can be associated with an infusion pump 434 and an infusion pump stand 432. The hyperosmotic liquid can be delivered to the subject 402 from the infusion pump 434 systemically through an infusion line 436 or conduit. However, other means of providing for infusion of the hyperosmotic fluid are also contemplated herein.

Therapeutic Agents

Various therapeutic agents can be administered in accordance with embodiments herein. In some embodiments, the therapeutic agent can be small molecule therapeutic agent. In other embodiments, the therapeutic agent can be a non-small molecule therapeutic agent, such as biologics. Therapeutic agents can include, but are not limited to, gene therapy agents, proteins (including, but not limited to, natural proteins, recombinant therapeutic proteins, antibodies, and the like), sugars, nucleic acids (including, but not limited to, natural nucleic acids, recombinant nucleic acids, vectors, and the like) and combinations of the same. Vectors can include, but are not limited to, plasmids, viral vectors, cosmids, and artificial chromosomes.

In some embodiments, the therapeutic agent can include a polynucleotide. In some embodiments, the therapeutic agent can include a recombinant polynucleotide. In some embodiments, the therapeutic agent can include a vector comprising a recombinant polynucleotide, including but not limited to vectors described above.

In some embodiments, the therapeutic agent can include a viral vector comprising a recombinant polynucleotide, including but not limited to vectors described above. Viral vectors can include, but are not limited to, recombinant retroviruses, recombinant lentiviruses, recombinant adenoviruses, and recombinant adeno-associated viruses. In some embodiments the therapeutic agent can specifically include an adeno-associated virus (AAV) vector.

While not intending to be bound by theory, it is believed that AAV vectors can be beneficial because AAV is highly efficient at transducing CNS cells; AAV vectors have demonstrated long-term (>8 years) expression in the CNS; AAV vectors have a small viral capsids with a diameter of 20 to 25 nanometers allowing better passage within the brain extracellular space. In addition, wild-type AAV is not known to cause disease and the transgene delivered from an AAV vector generally does not integrate into the host genome, which reduces concern of carcinogenesis.

In some embodiments, the therapeutic agent can include at least one selected from the group of proteins (including recombinant proteins and antibodies), anti-sense RNA, siRNA, and RNAi.

The specific dosages of the therapeutic agents can vary based on the nature of the condition to be treated and the activity of the therapeutic agent itself. In various embodiments, a therapeutically effective amount of the therapeutic agent is administered.

The therapeutic agent can be formulated with a carrier in order to provide sufficient volume for effective delivery. It will be appreciated that many different carriers can be used. In various embodiments, the carrier is an isotonic liquid, such as an isotonic aqueous liquid. The carrier can include various salts, sugars, sugar alcohols, and other compounds including, but not limited to, buffers. In some embodiments, the active agent carrier fluid can include the same components as described elsewhere herein regarding artificial or synthetic CSF fluid. The total volume of the therapeutic agent and the carrier liquid can be sufficient to allow for ease of injection at the desired site.

CSF Spaces

As described above, in various embodiments a therapeutic agent is injected or otherwise administered to a first CSF region or space. In addition, fluid communication is established between a second CSF region or space and a fluid reservoir. Cerebrospinal fluid (CSF) is a clear, colorless body fluid found in the brain and spine. The CSF occupies the subarachnoid space (between the arachnoid mater and the pia mater) and the ventricular system (a set of four interconnected cavities or ventricles in the brain). It constitutes the content of the ventricles, cisterns and sulci of the brain, as well as the central canal of the spinal cord. As used herein the term "CSF region" or "CSF space" shall refer to the region of a subject's anatomy that, under normal circumstances, is filled with cerebrospinal fluid.

It will be appreciated that the first CSF region (the region where the therapeutic agent is injected or otherwise administered) and the second CSF region (the region that is in fluid communication with the fluid reservoir) can be different physical locations. However, in some embodiments, the first CSF region and the second CSF region can be the same physical location. For example, in some embodiments, the area where the therapeutic agent is injected or administered can be the same general area that where fluid communication is established with the fluid reservoir and in other embodiments those two areas can be different.

In some embodiments, the first and second CSF regions can be selected from the group consisting of the cerebroventricular, cisternal, or intrathecal spaces (including, but not limited to the lumbar intrathecal space).

In some embodiments, the area where the therapeutic agent is injected or otherwise administered (first CSF region), is selected from the group consisting of the cerebroventricular and cisternal spaces. In some embodiments, the therapeutic agent can be injected simultaneously or sequentially in multiple different sites.

In some embodiments, the area where fluid communication is established with the fluid reservoir (second CSF region) is the intrathecal space (including, but not limited to the cisternal and/or lumbar intrathecal space). In some embodiments, fluid communication between the CSF region(s) and the fluid reservoir can be at multiple different sites.

Fluid Reservoir and Fluids

In some embodiments, the fluid reservoir includes a fluid that can be drawn from the reservoir and into the second CSF region. The fluid can include various biocompatible fluids. The fluid can include various dissolved solutes therein in various concentrations. In some embodiments, the fluid in the fluid reservoir can be isotonic or hypotonic. While not intending to be bound by theory, in view of a desired to create a current across the blood brain barrier, it is believed that the use of isotonic or hypotonic fluids in the fluid reservoir can be more effective than hypertonic fluids.

In some embodiments, the fluid reservoir can include a fluid having an osmolality of less than or equal to about 300, 295, 290, 285, 280, 275, 270, 265, 260, 255, 250, 245, 240, 235, 230, 225, 220, 210, 200, or 190 mOsm/kg $H_2O$. In some embodiments, the fluid can have an osmolality in a range wherein any of the foregoing values can serve as the upper or lower bound of the range, provided that the upper bound is greater than the lower bound. In a particular embodiment, the fluid reservoir can include a fluid having an osmolality of less than or equal to about 285 mOsm/kg $H_2O$.

In some embodiments, the fluid reservoir can include an aqueous saline solution as the fluid. In some embodiments, the aqueous saline solution can include from about 0.6% (by weight) to about 1.2% (by weight) saline. In some embodiments, the fluid can be about 0.9% saline. In some embodiments, the fluid can be a lactated Ringer's solution. In some embodiments an artificial or synthetic cerebrospinal fluid.

Many different specific formulations for artificial or synthetic cerebrospinal fluids are contemplated. In one example, 119 mM NaCl, 26.2 mM NaHCO$_3$, 2.5 mM KCl, 1 mM NaH$_2$PO$_4$, 1.3 mM MgCl$_2$, 10 mM glucose are mixed (in those proportions, but with the total amounts dictated based on the desired final value for mOsm/kg H$_2$O). This mixture can then be sparged with a gas mixture of 5% CO$_2$/95% 0$_2$ for 10-15 min, then 2.5 mM CaCl$_2$ can be added (again, as proportioned based on the desired final value for mOsm/kg H$_2$O). Synthetic or artificial cerebrospinal fluid are also available commercially, such as from Tocris Bioscience, Bristol U.K (Cat. No. 3525).

In some embodiments, the fluid reservoir can initially contain an amount of fluid sufficient to accommodate an expected amount of fluid to be drawn into the second CSF region, allowing for some reasonable safety factor. In some embodiments, the fluid reservoir contains an amount of fluid equivalent to at least about 10, 15, 20, 25, 30, 35, 40, or 45% or more of the subject's total cerebrospinal fluid. In some embodiments, the fluid reservoir contains an amount of fluid equivalent to at least about 25% of the subject's total cerebrospinal fluid. The following table (Table 1) shows approximate cerebrospinal fluid volumes for a variety of species of possible subjects.

TABLE 1

| Common Name | Body Weight (kg) | CSF Volume (ml) | CSF Synthesis (ml/h) | Brain (g) | Scale-up from Mouse |
|---|---|---|---|---|---|
| Mouse | 0.025 | 0.035 | 0.018 | .7 | 1 |
| Rat | 0.3 | 0.275 | 0.18 | 2 | 3 |
| Cat (domestic) | 4 | 5 | 1.2 | 30 | 50 |
| Dog (beagle) | 20 | 50 | 3 | 70 | 100 |
| Sheep | 40 | 35 to 50 | 4 to 11 | 140 | 200 |
| Human (new born) | 4 | 50 | — | 350-400 | 500 |
| Human (adult) | 70 | 150 | 20-30 | 1300-1400 | 2000 |

In some embodiments, the fluid reservoir can contain at least about 10, 20, 30, 40, 50, 60, 70, 80, 90, 100, 110, 120, 130, 140, 150, 160, 170, 180, 190, 200, 210, 220 ml or more of fluid.

In some embodiments, the fluid in the fluid reservoir can be maintained so as to have a hydraulic pressure at or above the baseline intracranial pressure. In particular, the fluid in the fluid reservoir can be maintained such that at the point wherein the fluid is drawn into the second CSF region, the hydraulic pressure is maintained at or above a baseline intracranial pressure.

In some embodiments, the fluid in the fluid reservoir can be maintained so as to have a hydraulic pressure at or above a central venous pressure. In particular, the fluid in the fluid reservoir can be maintained such that at the point wherein the fluid is drawn into the second CSF region, the hydraulic pressure is maintained at or above a central venous pressure.

In some embodiments, the fluid can be maintained so as to have a hydraulic pressure from about 5 cm to about 20 cm H$_2$O or from about 10 cm to about 15 cm H$_2$O above central venous pressure, and at or above the baseline intracranial pressure.

While not intending to be bound by theory, it is believed that it can be detrimental if the fluid is maintained at a hydraulic pressure that is too high above intracranial pressure. In specific, higher pressures can lead to accelerating losses of CSF fluid from drainage via the arachnoid villa.

It will be appreciated that the hydraulic pressure of the fluid within the fluid reservoir can be maintained and/or elevated in various ways. By way of example, in some embodiments, the reservoir is physically elevated to increase the hydraulic pressure of the exogenous cerebrospinal fluid. In some embodiments, a pump can be included. The pump can be in fluid communication with the reservoir and the pump can serve to increase the hydraulic pressure of the fluid within the reservoir.

Hyperosmotic Fluids

A hyperosmotic fluid can be infused systemically. In some embodiments, the hyperosmotic fluid can have an osmolality of greater than about 400, 500, 600, 700, 800, 900, 1000, 1100, 1200 or 1300 mOsm/kg H$_2$O. In some embodiments, the hyperosmotic fluid can have an osmolality in a range wherein any of the foregoing amounts can serve as the upper or lower bound of the range. In some particular embodiments, the hyperosmotic fluid can have an osmolality of greater than about 1000 mOsm/kg H$_2$O.

The hyperosmotic fluid can include various solutes. In some embodiments, the hyperosmotic fluid can include a sugar alcohol as a solute. In some embodiments, the hyperosmotic fluid can include at least one of mannitol and arabinose in an aqueous solution. In some embodiments, the hyperosmotic fluid can include 10, 15, 20, or 25 wt. % or more mannitol.

The amount (dose) of the hyperosmotic fluid infused can vary. For example, in the context of mannitol, a dose can be infused of at least about 0.5, 1.0, 1.5, 2.0, 2.5, 3.0, 3.5, 4.0, 4.5, 5.0, 5.5, or 6.0 g mannitol per kg of body weight. In some embodiments, a dose of mannitol is infused in the range of about 0.5 g mannitol per kg of body weight and 4 g mannitol per kg of body weight.

The dose of hyperosmotic fluid can be infused over various time frames. In some embodiments, the dose can be infused over a period of 5, 10, 15, 20, 25, 30, 35, 40, 45, 50, 60, 70, 80, or 90 minutes. In some embodiments, a dose of mannitol is infused over a time period of 10 to 30 minutes.

The specific site for infusion of the hyperosmotic fluid can vary. In some embodiments, the hyperosmotic fluid is infused into the carotid artery. In some embodiments, the hyperosmotic fluid is infused intravenously. Other sites for infusion are also contemplated herein.

Kits

In various embodiments, a kit is included herein. The kit can include any of the components described above. The kit can include some or all of the components for executing a method described herein. In some embodiments, the kit can include a first reservoir, a first fluid configured to be disposed within the first reservoir. The first fluid can be such as those described above. In some embodiments, the first fluid can be isotonic or hypotonic. The kit can further include an instrument for injecting a therapeutic agent into a first CSF space. Examples of suitable instruments are described above. The kit can further include a conduit for providing fluid communication between the first reservoir and a second CSF space. In some embodiments, the conduit can be an intrathecal catheter. The kit can further include a second reservoir and a second fluid configured to be disposed within the second reservoir. The second fluid can be as those described above. The second fluid can be hyperosmotic.

In various embodiments, a system is included herein. The system can include any of the components described above. The system can include some or all of the components for executing a method described herein. For example, in an embodiment, a system is included having a first reservoir and a first fluid disposed within the first reservoir, wherein the first fluid is isotonic or hypotonic. The system can further include a conduit for providing fluid communication between the first reservoir and a second CSF space. The system can further include a second reservoir and a second fluid disposed within the second reservoir, wherein the second fluid is hyperosmotic.

Material Preparation Example

Artificial Cerebrospinal Fluid: Sterile and oxygenated artificial CSF (aCSF) can be prepared with a final osmolality of approximately 280 mOsm/kg. The Cold Spring Harbor formulation for aCSF can be used and prepared as follows:

1. Mix:

| | |
|---|---|
| NaCl | 119.0 mM |
| NaHCO3 | 26.2 mM |
| KCl | 2.5 mM |
| NaH2PO4 | 1.0 mM |
| MgCl2 | 1.3 mM |
| glucose | 10.0 mM |

2. Gas with 5% CO2/95% O2 for 20 min, then add 2.5 mM CaCl2.
3. Using an osmometer, gradually add additional sterile water to reduce the osmolality to 280 mOsm/kg.
4. Filter sterilize with a 0.22-μm filter apparatus (and autoclave at 250° C.?), and store at 4° C. Note that the aCSF is stable for 3 wk. If older than 3 weeks, or if overt contamination (solution becomes cloudy) or precipitation is apparent, discard, and make fresh aCSF.
5. The solution can be oxygenated for at least 20 minutes within 4 hours of use.

IV Mannitol: The 25% mannitol solution can be warmed to approximately 37° C. and mixed to eliminate any sign of crystallization and mix. The solution can be held at approximately 37° C. prior to use.

Syringe and Catheter Preparation: Four syringes are to be prepared as described below and illustrated in FIG. 8. All preparations are to use sterile procedures.

aCSF Syringe: An aCSF syringe can be prepared as follows:

1. Draw 80 μL or more of oxygenated artificial CSF into a 100 μL pump-compatible syringe with a 30-gauge needle (e.g., Hamilton Models 7638-01 Syringe, 7803-07 #3 blunt 50 mm small hub replaceable needle (RN), and 14906 Syringe Guide).
2. Label syringe as "aCSF".
3. Insert the syringe needle into one end of a 30-cm length of sterile PE10 tubing. (Note: PE10 tubing with 0.61 mm OD×0.28 mm ID has a volume of approximately 0.616 μL/cm.)
4. Break a long non-coring tip 30-gauge dental needle from the hub using a needle holder.
5. Prepare a cannula by inserting the broken end of the needle approximately 3 mm into the other end of the 30-cm length PE10 tubing.
6. Prime tubing and cannula with aCSF from the syringe leaving no less than 50 μL of aCSF in the syringe.
7. Make a thin "Sharpie" mark on the PE10 tubing precisely 19.0 cm from the proximal end of the cannula needle. Note that the PE10 tubing has a calculated volume of 0.616 μL/cm and a 25 mm 30 gauge dental needle has a volume of 0.18 μL/cm.

Mannitol Syringe: A mannitol syringe can be prepared as follows:

1. Draw 200 μL or more of 25% mannitol into a 250 μl pump-compatible syringe with 26-gauge needle (e.g., Hamilton Models 7639-01 Syringe and 7806-03 #3 blunt 50 mm large hub RN).
2. Label syringe as "IV mannitol".
3. Insert the syringe needle into the proximal end of a polyethylene SAI MTV-PE1 tail vein catheter.
4. Make a thin "Sharpie" mark on the tail vein catheter precisely 5.0 cm proximal of the 1 F to PE25 tubing transition.
5. Prime the complete catheter with the 25% mannitol from the syringe leaving no less than 160 μL in the syringe.
6. Until the time of tail vein insertion, keep syringe and catheter warm at approximately 37° C. to avoid formation of crystals in the syringe and catheter.

Saline Flush Syringe: A saline syringe can be prepared as follows:

1. Draw ~15 μL of sterile 0.9% NaCl solution into a 100 μL syringe with a 26-gauge needle (e.g., Hamilton Models 7638-01 Syringe and 7804-03 #3 blunt 50 mm small hub RN).
2. Label syringe as "Saline".

IV Vector Syringe: An IV vector syringe can be prepared as follows:

1. Draw IV vector from the cohort selected IV tube precisely to the 100 μL mark of a 100 μL syringe with a 26-gauge needle (e.g., Hamilton Models 7638-01 Syringe, 7804-03 #3 blunt 50 mm small hub RN, and 14906 Syringe Guide).
2. Label syringe as "IV Vector".

Alternative Therapeutic Agent Delivery Example

Figure 7:
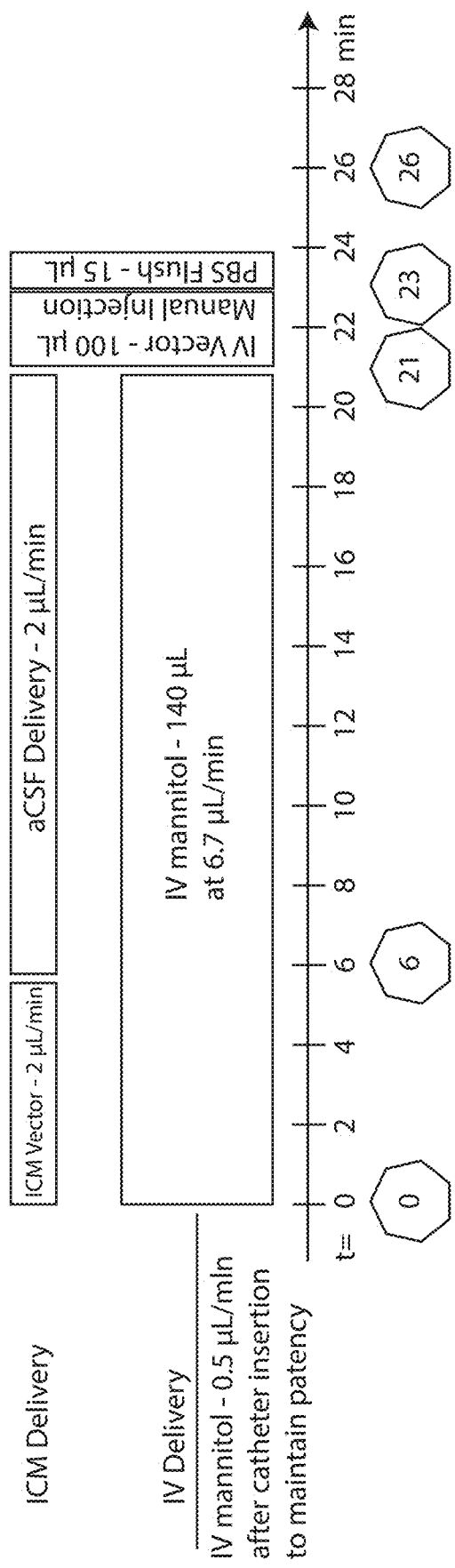
FIG. 7 is a delivery timeline example in accordance with various embodiments herein.
Figure 8:
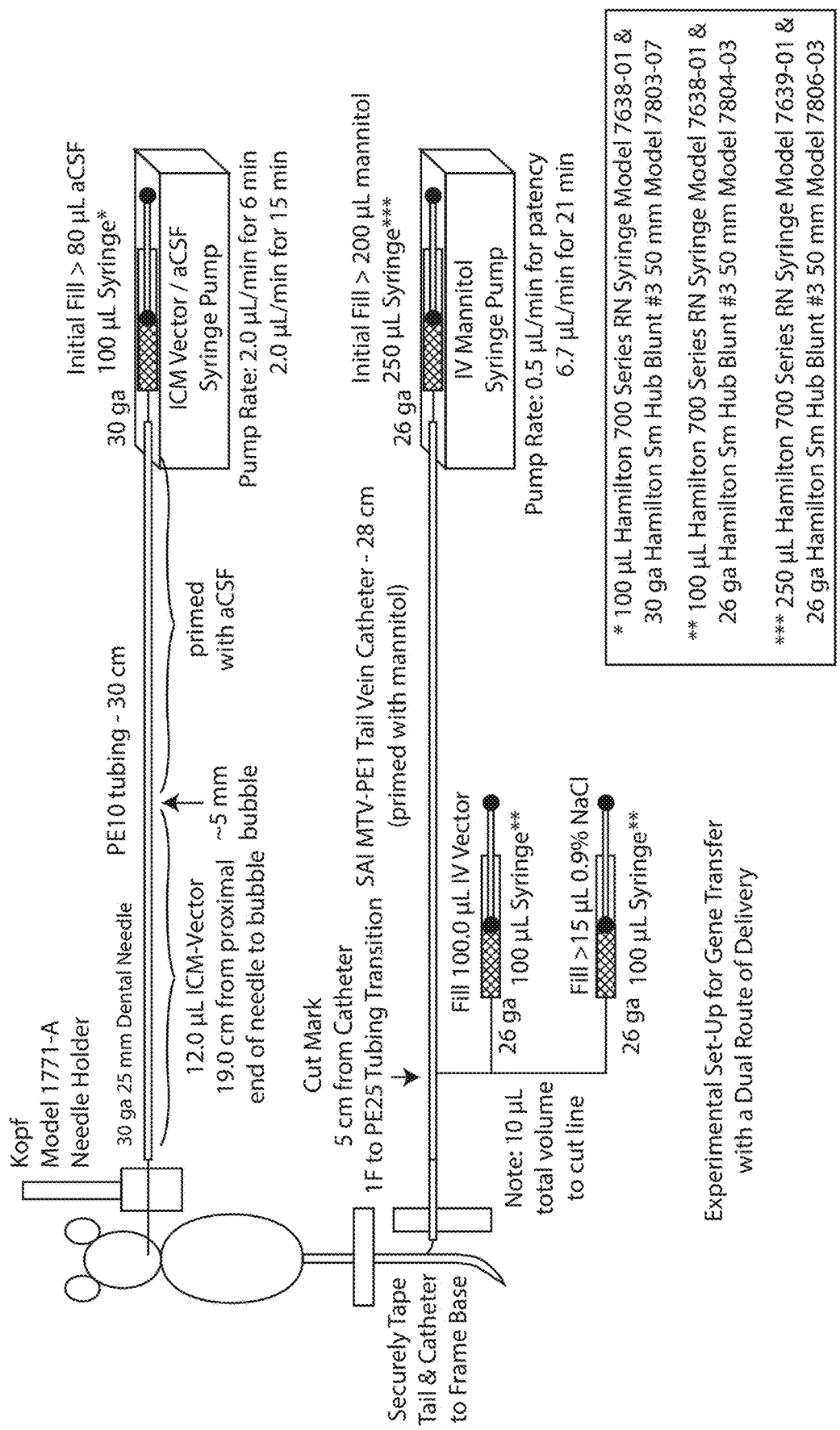
FIG. 8 is schematic illustration a set-up for a delivery system and method in accordance with various embodiments herein.

In various embodiments, therapeutic agent delivery can be accomplished using the steps shown below (referencing FIGS. 7 and 8). It will be appreciated that while aspects in this example are directed to a murine delivery scenario, that the principles and steps are also applicable to other subjects including humans. The specifics provided are only by way of example and shall not be construed in a limiting fashion.

1. Administer 0.5-1 ml lidocaine/bupivacaine (1 mg/ml and 0.25 mg/ml, respectively) subcutaneously at the incision site. Administer buprenorphine (0.05 mg/kg; subcutaneous) for post-surgical analgesia.
2. Make a sagittal incision of the skin inferior to the occiput. Use cotton swabs or eye spears to control any resultant bleeding.
3. Using the occipital crest as a reference point, pull apart the superficial connective tissue to expose the neck muscles below. Separate the muscles at the midline by carefully running the forceps down the middle of the incision site in the anterior-to-posterior axis. With a pair of curved forceps in each hand, join the tips in the middle near the bottom of the skull and pull the muscles aside. NOTE: This should expose the CM, which appears as a tiny inverted triangle, outlined by the cerebellum above and medulla below, behind the translucent dura membrane.
4. Using a surgical eye spear or sterile cotton swab, wipe the dura membrane covering the CM.
5. Select the vector tube marked "X" containing 12 μL of volume, where "X" is the cohort designation drawn in the randomization. Add 4.0 μL of sterile water to the tube to reduce the osmolality to approximately 290 mOsm/kg. Pipette the tube contents up and down a few times to mix.

6. Insure that the previously primed tubing and cannula connected to the aCSF syringe are completely filled with aCSF.
7. Keeping the distal end of the tubing/cannula sterile, position the "aCSF" syringe into a second syringe pump.
8. To avoid contamination of the ICM vector tube with aCSF, insert an air bubble of approximately 0.5 cm into the cannula by withdrawing approximately 0.3 μL with the aid of the syringe pump.
9. Insert the ICM cannula needle into the ICM vector tube (from prior step) and withdraw precisely 12 μL of the vector into the tubing using the syringe pump. (Note: This should result in the air bubble being located at the mark made during syringe/cannula preparation Step 8a, and confirm that there is no more than about 4 μL remaining in the ICM vector tube.)
10. Position a Kopf Model 1771-A-Mod Electrode Holder with Straight Clamp onto the stereotactic frame. (Note: This holder is modified with a pad for holding needles from 0.092 to 2.325 mm diameter. A 30 G needle has a diameter of 0.31 mm.) Align the holder to be at a 45-degree angle relative to the mouse head and roughly aligned with the center of the cisterna magna.
11. Firmly secure the ICM cannula needle in the Model 1771-A holder with approximately 1 cm of the cannula needle extending below the holder to allow visibility of the tip of the needle. Align the holder such that the needle is positioned at a 45-degree angle to the mouse head and then adjust the position of the needle tip to be in direct contact with the dura over the center of the cisterna magna.
12. While observing the cisterna magna under magnification, use the stereotactic manipulation to extend the needle bevel tip ~2 mm so as to puncture the dura and enter the cisterna magna. Ensure that the needle is only inserted to a depth of 1-2 mm below the dura.
13. If necessary, dry off any CSF leak upon penetration using a surgical eye spear or sterile cotton swabs.
14. Record the volume of mannitol in the "IV mannitol" syringe.
15. Deliver the ICM vector by programming the "aCSF" syringe pump to deliver 2.0 μl per minute for six minutes and simultaneously Increase the rate of IV mannitol delivery through the tail vein needle by programming the associated pump to deliver 6.7 μL per minute.
16. Watch and note if any leakage occurs adjacent to the needle entry into the cisterna magna. (Note: If any leakage is observed during the pilot sessions, the procedure may need to be modified.)
17. Note when all of the vector and the bubble have been delivered into the cisterna magna and record the volume of aCSF in the "aCSF" syringe.
18. Continue the IV mannitol delivery through the tail vein needle by programming the associated pump to deliver 6.7 μL per minute for 15 minutes. Continue the delivery of aCSF through the cisterna magna needle with a delivery rate of 2.0 μL per minute over the same 15-minute period. See FIG. 1. (Note: If leakage is observed during the pilot runs, the delivery rate may need to be adjusted.)
19. Record the final volume of aCSF in the "aCSF" syringe and the final volume of mannitol in the "IV mannitol" syringe in the Data Summary.

Alternative IV Therapeutic Agent Delivery Example

In various embodiments, therapeutic agent delivery can be accomplished using the steps shown below (referencing FIGS. 7 and 8). It will be appreciated that this can be in conjunction with the "Alternative Therapeutic Agent Delivery Example" referenced above. It will be appreciated that while aspects in this example are directed to a murine delivery scenario, that the principles and steps are also applicable to other subjects including humans. The specifics provided are only by way of example and shall not be construed in a limiting fashion.

1. At the end of the 15-minute delivery of IV mannitol and artificial CSF into the cisterna magna, stop both pumps.
2. Place a clamp ~1 cm distal to the "cut mark" made on the catheter in Step 8b.
3. Cut the tail vein catheter just distal to the "cut mark".
4. Insert the "IV Vector" syringe needle into the tail vein cannula and release the clamp. Within one minute from the end of the IV mannitol infusion, manually deliver 100 μl of vector.
5. Reposition the clamp. Replace the "IV Vector" syringe with the "Saline" syringe and remove the clamp.
6. Flush the tail vein catheter with a 15 μl bolus of sterile 0.9% NaCl from the "Saline" syringe. (Note: The amount of the bolus may need to change based on the desired length of the tail vein cannula catheter determined during the pilot sessions.)

An exemplary delivery timeline is as follows (referencing FIG. 7):

Delivery Timeline: The "IV mannitol" syringe pump is to be programmed to a rate of approximately 0.5 μL/min to maintain tail vein catheter patency. The remaining timeline transitions are shown in minutes from the start of the ICM vector delivery:

0.0 Start ICM Vector/aCSF pump to deliver the ICM vector at a rate of 2.0 μL/min for ~6 minutes to deliver 12 μL of ICM vector and the air bubble and then for an additional 15 minutes to deliver the aCSF.

0.0 At the start of the ICM vector delivery, increase the IV mannitol pump from a background rate of 0.5 μL/min to a rate of 6.7 μL/min for the period of ICM vector delivery plus an additional 15 minutes.

21.0 Turn off both the IV mannitol pump and the aCSF pump. Place a clamp on the tail vein catheter approximately 1 cm from the cut mark towards the mouse. Cut the tail vein catheter just distal to the cut mark. Insert the IV vector syringe needle into the catheter, release the clamp, and deliver 100 μL of the IV vector.

23.0 Reapply the tail vein catheter clamp, remove the IV vector syringe needle from the catheter, insert the PBS syringe, remove the clamp, and deliver 15 μL of PBS to completely flush the catheter of vector.

26.0 Back out the ICM needle and close ICM incision. Remove tail vein catheter.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A method of administering a therapeutic agent to a central nervous system (CNS) of a subject comprising:
   injecting a therapeutic agent into a first cerebrospinal fluid (CSF) region of the subject;
   infusing a hyperosmotic fluid systemically causing an osmotic pressure across the blood brain barrier which results in a net flow of fluid outward across the blood brain barrier; and
   providing flow of an isotonic or hypotonic fluid into a second cerebrospinal fluid (CSF) region that partially or fully replaces the net flow of fluid outward across the blood brain barrier;
   wherein the flow of the isotonic or hypotonic fluid into the second CSF region does not increase the intracranial pressure above a baseline intracranial pressure;
   the therapeutic agent comprising a biologic agent.

2. The method of claim 1, wherein injecting the therapeutic agent into the first cerebrospinal fluid (CSF) region of the subject and injecting the isotonic or hypotonic fluid into the second cerebrospinal fluid (CSF) region are performed using the same conduit.

3. The method of claim 1, further comprising injecting a second therapeutic agent systemically.

4. The method of claim 1, the hyperosmotic fluid comprising mannitol.

5. The method of claim 1, the isotonic or hypotonic fluid comprising an artificial cerebrospinal fluid.

6. The method of claim 1, the isotonic or hypotonic fluid comprising an oxygenated fluid.

7. The method of claim 1, wherein the infusion of the hyperosmotic fluid and the injection of the isotonic or hypotonic fluid overlap at least partially.

8. The method of claim 1, wherein the first CSF region and the second CSF region are different.

9. The method of claim 1, wherein the first CSF region and the second CSF region are the same.

10. The method of claim 1, the first and second CSF regions selected from the group consisting of the cerebroventricular, cisternal, or intrathecal spaces.

11. The method of claim 1, wherein the hyperosmotic fluid is infused intravascularly.

12. The method of claim 1, the therapeutic agent comprising a polynucleotide.

13. The method of claim 1, the therapeutic agent comprising a vector comprising a recombinant polynucleotide.

14. The method of claim 1, the therapeutic agent comprising an adeno-associated virus (AAV) vector.

15. The method of claim 1, the therapeutic agent comprising at least one selected from the group of antibodies, proteins, anti-sense nucleic acids and RNA.

16. The method of claim 1, the therapeutic agent comprising a non-small molecule agent.

17. The method of claim 1, wherein the step of injecting the therapeutic agent into the first cerebrospinal fluid (CSF) region of the subject is performed before or during the step of infusing the hyperosmotic fluid systemically.

* * * * *